United States Patent

Takano

[11] Patent Number: 6,114,286
[45] Date of Patent: Sep. 5, 2000

[54] PYRIMIDINONE DERIVATIVES

[75] Inventor: Minoru Takano, Kameoka, Japan

[73] Assignee: Sumitomo Chemical Company, Limited, Osaka, Japan

[21] Appl. No.: 09/277,603

[22] Filed: Mar. 29, 1999

[30] Foreign Application Priority Data

Mar. 30, 1998 [JP] Japan ................. 10-083533

[51] Int. Cl.[7] .............. A01N 43/54; A01N 43/90; C07D 487/00; C07D 239/70
[52] U.S. Cl. ............ 504/240; 504/241; 544/281; 544/282
[58] Field of Search ............... 504/240, 241; 544/281, 282

[56] References Cited

U.S. PATENT DOCUMENTS 5,683,966  11/1997  Konz ........................... 504/243

FOREIGN PATENT DOCUMENTS

| 0568041-A1 | 4/1993 | European Pat. Off. . |
| 0902029-A1 | 3/1999 | European Pat. Off. . |
| 2133998 | 1/1973 | Germany . |
| 97/35845 | 10/1997 | WIPO . |
| 98/14452 WO | 4/1998 | WIPO . |
| 98/14452-A1 | 4/1998 | WIPO . |

OTHER PUBLICATIONS

Kenzo Sirakawa: *Studies on Pyrimidine Derivatives. X. N–Benzyl–s–triazolopyrimidinones*, Mar. 25, 1960, Yakugaku Zasshi vol. 80, p1550–1556.

Jozsef Reiter, Laszlo Pongo, and Peter Dvortsak: *On Traiazoles*XI[1]*Structure Elucidation of Isomeric 1,2,4 Triazolopyrimidinones*[2] Tetrahedron vol. 43, No. 11, pp. 2497 to 2504, 1987.

Chemical Abstracts, vol. 54, No. 2, Nov. 25, 1960 (XP002110786) Abstract No. 24762f.

Chemical Abstracts, vol. 55, No. 11, May 29, 1961 (XP002110787). Abstract No. 10452h.

A. H. Beckett et al., Tetrahedron, vol. 24, No. 19, 1968, pp. 2839–2850. Abstract No. 79–104714B.

Derwent Publications, Ltd. (XP002110788), for JP 54–005035–A, Jan. 16, 1979.

*Primary Examiner*—Mukund J. Shah
*Assistant Examiner*—Ben Schroeder
*Attorney, Agent, or Firm*—Birch, Stewart, Kolasch & Birch, LLP

[57] ABSTRACT

The present invention provides new pyrimidinone derivative encompassed by the formula:

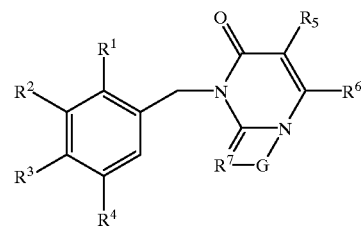

wherein, $R^1$, $R^2$, $R^3$, $R^4$, $R^5$, $R^6$, $R^7$ and G are as defined in the specification. The pyrimidinone derivatives exhibit excellent herbicidal efficacy, therefore, the pyrimidinone derivatives can be used as an active ingredient for herbicidal compositions and can be utilized in herbicidal methods, which are also discussed.

18 Claims, No Drawings

PYRIMIDINONE DERIVATIVES

FIELD OF THE INVENTION

The present invention relates to pyrimidinone derivatives having excellent herbicidal activity and the use thereof.

SUMMARY OF THE INVENTION

The present inventor has intensely studied to seek out compounds that have excellent herbicidal activity, and has found that pyrimidinone derivatives encompassed by Chemical Formula 3, below, posses an excellent herbicidal activity, and arrived at the present invention. Accordingly, the present invention provides pyrimidinone derivatives encompassed by Chemical Formula 3 (hereinafter, the present invention compound) and a herbicidal method that employs said pyrimidinone derivatives.

[Chemical Formula 3]

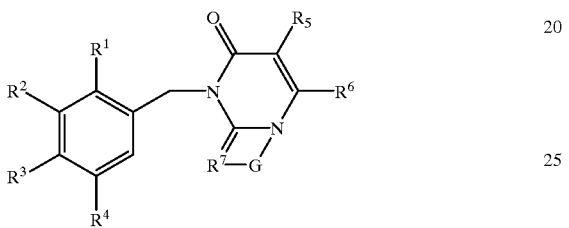

wherein, $R^1$ represents hydrogen, halogen, $C_1$–$C_3$ alkyl or $C_1$–$C_3$ haloalkyl;

$R^2$ represents hydrogen, halogen, $C_1$–$C_6$ alkyl, $C_1$–$C_6$ haloalkyl, $OR^8$, $SR^9$, $NHR^{10}$, $COOR^{11}$, $COR^{12}$, $SO_2R^{13}$, $NO_2$ or $CN$;

$R^3$ represents hydrogen, halogen, $C_1$–$C_6$ alkyl, $C_1$–$C_6$ haloalkyl, $C_1$–$C_3$ alkoxy $C_1$–$C_3$ alkyl, $OR^8$, $SR^9$, $NHR^{10}$, $COOR^{11}$, $COR^{12}$, $SO_2R^{13}$, $C(R^{12})=C(R^{14})(R^{15})$, $NO_2$ or $CN$;

$R^4$ represents hydrogen, halogen, $C_1$–$C_6$ alkyl, $C_1$–$C_6$ haloalkyl, $C_1$–$C_3$ alkoxy $C_1$–$C_3$ alkyl, $OR^8$, $SR^9$, $NHR^{10}$, $COOR^{11}$, $COR^{12}$, $SO_2R^{13}$, $CH=C(R^{14})(R^{15})$, $C(R^{16})=NOR^{17}$, $NO_2$ or $CN$;

$R^5$ represents hydrogen, halogen or $C_1$–$C_3$ alkyl;

$R^6$ represents $C_1$–$C_3$ alkyl or $C_1$–$C_3$ haloalkyl;

$R^7$ represents nitrogen or CH;

in which $R^8$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ halocycloalkyl, $C_3$–$C_{10}$ cycloalkenyl, $C_3$–$C_{10}$ halocycloalkenyl, $C_1$–$C_5$ alkylcarbonyl, $C_1$–$C_5$ haloalkylcarbonyl, $C_3$–$C_6$ cycloalkylcarbonyl, $C_3$–$C_6$ halocycloalkylcarbonyl, $C_1$–$C_6$ alkylcabonyl $C_1$–$C_6$ alkyl, $C_1$–$C_6$ haloalkylcarbonyl $C_1$–$C_6$ alkyl, $C_1$–$C_6$ alkylcabonyl $C_1$–$C_6$ haloalkyl, $C_1$–$C_6$ haloalkylcarbonyl $C_1$–$C_6$ haloalkyl, $C_1$–$C_6$ alkoxycarbonyl, $C_1$–$C_6$ haloalkoxycarbonyl, $C_3$–$C_{10}$ cycloalkoxycarbonyl, carboxy $C_1$–$C_5$ alkyl, $C_1$–$C_{10}$ alkyoxycarbonyl $C_1$–$C_5$ alkyl, $C_1$–$C_{10}$ haloalkoxycarbonyl $C_1$–$C_5$ alkyl, $C_1$–$C_{10}$ alkoxycarbonyl $C_1$–$C_5$ haloalkyl, $C_1$–$C_{10}$ haloalkoxycarbonyl $C_1$–$C_5$ haloalkyl, $C_3$–$C_{10}$ cycloalkoxycarbonyl $C_1$–$C_5$ alkyl, $C_3$–$C_{10}$ halocycloalkoxycarbonyl $C_1$–$C_5$ alkyl, $C_3$–$C_{10}$ halocycloalkoxycarbonyl $C_1$–$C_5$ haloalkyl, $C_3$–$C_{10}$ cycloalkoxycarbonyl $C_1$–$C_5$ haloalkyl, $C_1$–$C_6$ alkoxy $C_1$–$C_6$ alkyl, $C_1$–$C_6$ alkoxy $C_1$–$C_6$ haloalkyl, $C_1$–$C_6$ haloalkoxy $C_1$–$C_6$ alkyl, $C_1$–$C_6$ haloalkoxy $C_1$–$C_6$ haloalkyl, $C_1$–$C_6$ alkylthio $C_1$–$C_6$ alkyl, $C_1$–$C_6$ alkylthio $C_1$–$C_6$ haloalkyl, $C_1$–$C_6$ haloalkylthio $C_1$–$C_6$ alkyl, $C_1$–$C_6$ haloalkylthio $C_1$–$C_6$ haloalkyl, cyano $C_1$–$C_4$ alkyl, aryl that may have substituent(s), aryl $C_1$–$C_3$ alkyl that may have substituent(s) or arylcarbonyl that may have substituent(s);

$R^9$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ halocycloalkyl, $C_3$–$C_{10}$ cycloalkenyl, $C_3$–$C_{10}$ halocycloalkenyl, $C_1$–$C_5$ alkylcarbonyl, $C_1$–$C_5$ haloalkylcarbonyl, $C_3$–$C_6$ cycloalkylcarbonyl, $C_3$–$C_6$ halocycloalkylcarbonyl, $C_1$–$C_6$ alkylcabonyl $C_1$–$C_6$ alkyl, $C_1$–$C_6$ haloalkylcarbonyl $C_1$–$C_6$ alkyl, $C_1$–$C_6$ alkylcabonyl $C_1$–$C_6$ haloalkyl, $C_1$–$C_6$ haloalkylcarbonyl $C_1$–$C_6$ haloalkyl, $C_1$–$C_6$ alkoxycarbonyl, $C_1$–$C_6$ haloalkoxycarbonyl, $C_3$–$C_{10}$ cycloalkoxycarbonyl, carboxy $C_1$–$C_5$ alkyl, $C_1$–$C_{10}$ alkoxycarbonyl $C_1$–$C_5$ alkyl, $C_1$–$C_{10}$ haloalkoxycarbonyl $C_1$–$C_5$ alkyl, $C_1$–$C_{10}$ alkoxycarbonyl $C_1$–$C_5$ haloalkyl, $C_1$–$C_{10}$ haloalkoxycarbonyl $C_1$–$C_5$ haloalkyl, $C_3$–$C_{10}$ cycloalkoxycarbonyl $C_1$–$C_5$ alkyl, $C_3$–$C_{10}$ halocycloalkoxycarbonyl $C_1$–$C_5$ alkyl, $C_3$–$C_{10}$ halocycloalkoxycarbonyl $C_1$–$C_5$ haloalkyl, $C_3$–$C_{10}$ cycloalkoxycarbonyl $C_1$–$C_5$ haloalkyl, $C_1$–$C_6$ alkoxy $C_1$–$C_6$ alkyl, $C_1$–$C_6$ alkoxy $C_1$–$C_6$ haloalkyl, $C_1$–$C_6$ haloalkoxy $C_1$–$C_6$ alkyl, $C_1$–$C_6$ haloalkoxy $C_1$–$C_6$ haloalkyl, $C_1$–$C_6$ alkylthio $C_1$–$C_6$ alkyl, $C_1$–$C_6$ alkylthio $C_1$–$C_6$ haloalkyl, $C_1$–$C_6$ haloalkylthio $C_1$–$C_6$ alkyl, $C_1$–$C_6$ haloalkylthio $C_1$–$C_6$ haloalkyl, cyano $C_1$–$C_4$ alkyl, aryl that may have substituent(s), aryl $C_1$–$C_3$ alkyl that may have substituent(s), arylcarbonyl that may have substituent(s) or $SR^{18}$;

$R^{10}$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_5$ haloalkynyl, $C_3$–$C_{10}$ cycloalkyl, $C_3$–$C_{10}$ halocycloalkyl, $C_3$–$C_{10}$ cycloalkenyl, $C_3$–$C_{10}$ halocycloalkenyl, $C_1$–$C_5$ alkylcarbonyl, $C_1$–$C_5$ haloalkylcarbonyl, $C_3$–$C_6$ cycloalkylcarbonyl, $C_3$–$C_6$ halocycloalkylcarbonyl, $C_1$–$C_6$ alkylcabonyl $C_1$–$C_6$ alkyl, $C_1$–$C_6$ haloalkylcarbonyl $C_1$–$C_6$ alkyl, $C_1$–$C_6$ alkylcabonyl $C_1$–$C_6$ haloalkyl, $C_1$–$C_6$ haloalkylcarbonyl $C_1$–$C_6$ haloalkyl, $C_1$–$C_6$ alkoxycarbonyl, $C_1$–$C_6$ haloalkoxycarbonyl, $C_3$–$C_{10}$ cycloalkoxycarbonyl, carboxy $C_1$–$C_5$ alkyl, $C_1$–$C_{10}$ alkyoxycarbonyl $C_1$–$C_5$ alkyl, $C_1$–$C_{10}$ haloalkoxycarbonyl $C_1$–$C_5$ alkyl, $C_1$–$C_{10}$ alkoxycarbonyl $C_1$–$C_5$ haloalkyl, $C_1$–$C_{10}$ haloalkoxycarbonyl $C_1$–$C_5$ haloalkyl, $C_3$–$C_{10}$ cycloalkoxycarbonyl $C_1$–$C_5$ alkyl, $C_3$–$C_{10}$ halocycloalkoxycarbonyl $C_1$–$C_5$ alkyl, $C_3$–$C_{10}$ halocycloalkoxycarbonyl $C_1$–$C_5$ haloalkyl, $C_3$–$C_{10}$ cycloalkoxycarbonyl $C_1$–$C_5$ haloalkyl, $C_1$–$C_6$ alkoxy $C_1$–$C_6$ alkyl, $C_1$–$C_6$ alkoxy $C_1$–$C_6$ haloalkyl, $C_1$–$C_6$ haloalkoxy $C_1$–$C_6$ alkyl, $C_1$–$C_6$ haloalkoxy $C_1$–$C_6$ haloalkyl, $C_1$–$C_6$ alkylthio $C_1$–$C_6$ alkyl, $C_1$–$C_6$ alkylthio $C_1$–$C_6$ haloalkyl, $C_1$–$C_6$ haloalkylthio $C_1$–$C_6$ alkyl, $C_1$–$C_6$ haloalkylthio $C_1$–$C_6$ haloalkyl, cyano $C_1$–$C_4$ alkyl, aryl that may have substituent(s), aryl $C_1$–$C_3$ alkyl that may have substituent(s), arylcarbonyl that may have substituent(s), $SR^{18}$, $SOR^{19}$ or $SO_2R^{20}$;

$R^{11}$ represents hydrogen, $C_1$–$C_{10}$ alkyl, $C_1$–$C_{10}$ haloalkyl, $C_3$–$C_8$ cycloalkyl, $C_3$–$C_8$ halocycloalkyl, $N(R^{21})(R^{22})$ group, $N=C(R^{21})(R^{22})$ group, carboxy $C_1$–$C_3$ alkyl, $C_1$–$C_5$ alkoxycarbonyl $C_1$–$C_3$ alkyl, $C_1$–$C_5$ haloalkoxycarbonyl $C_1$–$C_3$ alkyl, $C_3$–$C_6$ cycloalkoxycarbonyl $C_1$–$C_3$ alkyl or $C_3$–$C_8$ alkenyloxycarbonyl $C_1$–$C_3$ alkyl;

$R^{12}$ represents hydrogen, chlorine, $C_1$–$C_5$ alkyl, $C_1$–$C_5$ haloalkyl, $C_3$–$C_6$ cycloalkyl, $C_3$–$C_6$ halocycloalkyl or $N(R^{23})(R^{24})$;

$R^{13}$ represents chlorine, $C_1$–$C_{10}$ alkyl, $C_1$–$C_{10}$ haloalkyl, $N(R^{25})(R^{26})$ or $OR^{27}$;

$R^{14}$ represents hydrogen, halogen or $C_1$–$C_3$ alkyl;

$R^{15}$ represents hydrogen, $COOR^{28}$ or $CN$;

$R^{16}$ represents hydrogen, halogen, $C_1$–$C_4$ alkyl, $C_1$–$C_4$ haloalkyl, $C_3$–$C_5$ cycloalkyl or $C_3$–$C_5$ halocycloalkyl;

$R^{17}$ represents hydrogen, $C_1$–$C_{10}$ alkyl, $C_1$–$C_{10}$ haloalkyl, $C_3$–$C_6$ cycloalkyl, $C_3$–$C_6$ halocycloalkyl, $C_3$–$C_5$ alkenyl, $C_3$–$C_5$ haloalkenyl, $C_3$–$C_5$ alkynyl, $C_3$–$C_5$ haloalkynyl, carboxy $C_1$–$C_3$ alkyl, $C_1$–$C_5$ alkoxycarbonyl $C_1$–$C_3$ alkyl, aryl that may have substituent(s) or aryl $C_1$–$C_3$ alkyl that may have substituent(s);

$R^{18}$ represents $C_1$–$C_{10}$ alkyl, $C_1$–$C_{10}$ haloalkyl or aryl that may have substituent(s);

$R^{19}$ represents $C_1$–$C_{10}$ alkyl, $C_1$–$C_{10}$ haloalkyl, $C_3$–$C_8$ cycloalkyl, $C_3$–$C_8$ halocycloalkyl or aryl that may have substituent(s);

$R^{20}$ represents $C_1$–$C_{10}$ alkyl, $C_1$–$C_{10}$ haloalkyl, $C_3$–$C_8$ cycloalkyl, $C_3$–$C_8$ halocycloalkyl or aryl that may have substituent(s);

$R^{21}$ represents hydrogen or $C_1$–$C_5$ alkyl;

$R^{22}$ represents hydrogen, $C_1$–$C_5$ alkyl, $C_1$–$C_5$ haloalkyl or aryl that may have substituent(s);

$R^{23}$ represents hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl or aryl that may have substituent(s);

$R^{24}$ represents hydrogen, $C_1$–$C_{10}$ alkyl, or $C_1$–$C_{10}$ haloalkyl;

$R^{25}$ represents hydrogen, $C_1$–$C_5$ alkyl or $C_1$–$C_5$ haloalkyl;

$R^{26}$ represents hydrogen, $C_1$–$C_{10}$ alkyl, or $C_1$–$C_{10}$ haloalkyl;

$R^{27}$ represents $C_1$–$C_{10}$ alkyl;

$R^{28}$ represents hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl or aryl that may have substituent(s); and G represents G-1, G-2, G-3, G-4 or G-5 given in Chemical Formula 4:

[Chemical Formula 4]

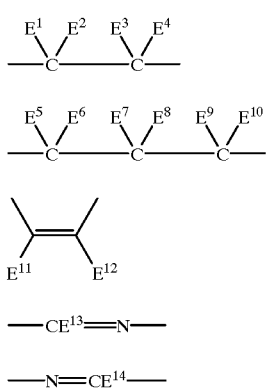

wherein $E^1$, $E^2$, $E^3$, $E^4$, $E^5$, $E^6$, $E^7$, $E^8$, $E^9$, $E^{10}$, $E^{11}$, $E^{12}$, $E^{13}$ or $E^{14}$ each represent hydrogen, halogen or $C_1$–$C_3$ alkyl.

DETAILED DESCRIPTION OF THE INVENTION

In the present invention,
in the definition of $R^1$,
halogen atom means fluorine, chlorine, bromine or iodine;

$C_1$–$C_3$ alkyl include methyl, ethyl, etc.; and $C_1$–$C_3$ haloalkyl include bromomethyl, chloromethyl, dichloromethyl, trichloromethyl, trifluoromethyl, pentafluoroethyl, 1,1-difluoroethyl, 3,3,3-trifluoropropyl, etc.;

in the definition of $R^2$,
halogen includes fluorine, chlorine, bromine or iodine;

$C_1$–$C_6$ alkyl includes methyl, ethyl, isopropyl, normal (hereinafter, n-) pentyl, etc.; and $C_1$–$C_6$ haloalkyl includes trichloromethyl, trifluoromethyl, chlorodifluoromethyl, pentafluoroethyl, etc.;

in the definition of $R^3$,
halogen means fluorine, chlorine, bromine or iodine;

$C_1$–$C_6$ alkyl includes methyl, ethyl, isopropyl, n-butyl, etc.;

$C_1$–$C_6$ haloalkyl includes chloromethyl, dichloromethyl, trichloromethyl, trifluoromethyl, chlorodifluoromethyl, pentafluoroethyl, 1,1-difluoroethyl, 1,1-difluorohexyl, etc.; and $C_1$–$C_3$ alkoxy $C_1$–$C_3$ alkyl includes methoxymethyl, methoxyethyl, ethoxymethyl, etc.;

in the definition of $R^4$,
halogen means fluorine, chlorine, bromine or iodine;

$C_1$–$C_6$ alkyl includes methyl, ethyl, isopropyl, n-butyl etc.;

$C_1$–$C_6$ haloalkyl includes chloromethyl, dichloromethyl, trichloromethyl, trifluoromethyl, chlorodifluoromethyl, pentafluoroethyl, 1,1-difluoroethyl, 3,3,3-trifluoropropyl, 5,5,5,1,1-pentafluoropentyl, etc.; and $C_1$–$C_3$ alkoxy $C_1$–$C_3$ alkyl includes methoxymethyl, methoxyethyl, ethoxymethyl, etc.;

in the definition of $R^5$,
halogen means fluorine, chlorine, bromine or iodine; and $C_1$–$C_3$ alkyl be a methyl, ethyl, etc.;

in the definition of $R^6$,
$C_1$–$C_3$ alkyl includes methyl, ethyl, etc.; and $C_1$–$C_3$ haloalkyl includes trichloromethyl, chlorodifluoromethyl, trifluoromethyl, pentafluoroethyl, 1,1-difluoroethyl, etc.;

in the definition of $R^8$,
$C_1$–$C_{10}$ alkyl includes methyl, ethyl, isopropyl, n-butyl, isopentyl, n-octyl, etc.;

$C_1$–$C_{10}$ haloalkyl includes 2-fluoroethyl, 2,2,2-trifluoroethyl, 5-chloro-n-pentyl, 7-bromoheptyl, etc.;

$C_3$–$C_8$ alkenyl includes allyl, 1-methyl-2-propenyl, 3-butenyl, 2-butenyl, 3-methyl-2-butenyl, 2-methyl-3-butenyl, etc.;

$C_3$–$C_8$ haloalkenyl includes 2-chloro-2-propenyl, 3,3-dichloro-2-propenyl, etc.;

$C_3$–$C_8$ alkynyl includes propargyl, 1-methyl-2-propynyl, 2-butynyl, 3-butynyl, 1,1-dimethyl-2-propynyl, etc.;

$C_3$–$C_8$ haloalkynyl includes 3-iodo-2-propynyl, 3-bromo-2-propynyl, etc.;

$C_3$–$C_{10}$ cycloalkyl includes cyclopropyl, cyclopentyl, cyclohexyl, 4,4-dimethylcyclohexyl, etc.;

$C_3$–$C_{10}$ halocycloalkyl includes 2-fluorocyclopentyl, 3,4-dichlorocyclohexyl, etc.;

$C_3$–$C_{10}$ cycloalkenyl includes 2-cyclohexenyl, 3-cyclohexenyl, etc.;

$C_3$–$C_{10}$ halocycloalkenyl includes 4-chloro-2-cyclohexenyl, etc.;

$C_1$–$C_5$ alkylcarbonyl includes acetyl, propionyl, etc.;

$C_1$–$C_5$ haloalkylcarbonyl includes trifluoroacetyl, dichloroacetyl, pentafluoropropionyl, etc.;

$C_3$–$C_6$ cycloalkylcarbonyl includes cyclopropylcarbonyl, cyclopentylcarbonyl, etc.;

$C_3$–$C_6$ halocycloalkylcarbonyl includes 2,2-difluorocyclopentylcarbonyl, etc.;

$C_1$–$C_6$ alkylcarbonyl $C_1$–$C_6$ alkyl includes 2-oxopropyl, 4-oxopentyl, 3-ethyl-2-oxooctyl, 5-methyl-4-oxohexyl, etc.;

$C_1$–$C_6$ haloalkylcarbonyl $C_1$–$C_6$ alkyl includes 3,3,3-trifluoro-2-oxopropyl, etc.;

$C_1$–$C_6$ alkylcarbonyl $C_1$–$C_6$ haloalkyl includes 1-chloro-3-methyl-2-oxobutyl, etc.;

$C_1$–$C_6$ haloalkylcarbonyl $C_1$–$C_6$ haloalkyl includes 2,7-difluoro-4-oxoheptyl, etc.;

$C_1$–$C_6$ alkyloxycarbonyl includes methoxycarbonyl, ethoxycabonyl, propoxycarbonyl, butoxycarbonyl, amyloxycarbonyl, iso-propoxycarbonyl, iso-butoxycarbonyl, iso-amyloxycarbonyl, etc.;

$C_1$–$C_6$ haloalkoxycarbonyl includes 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dichloroethoxycarbonyl, 2,2,2-trifluoroethoxycarbonyl, 2,2,2-trichloroethoxycarbonyl, 2,2,2-tribromoethoxycarbonyl, etc.;

$C_3$–$C_{10}$ cycloalkoxycarbonyl includes cyclobutyloxycarbonyl, cyclopentyloxycarbonyl, cyclohexyloxycarbonyl, etc.;

carboxy $C_1$–$C_5$ alkyl includes carboxymethyl, 1-carboxyethyl, 1-carboxy-1-methylethyl, etc.;

$C_1$–$C_{10}$ alkoxycarbonyl $C_1$–$C_5$ alkyl includes methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, 1-t-butoxycarbonylethyl, etc.;

$C_1$–$C_{10}$ haloalkoxycarbonyl $C_1$–$C_5$ alkyl includes 2-fluoroethoxycarbonylmethyl, 2,2,2-trifluoroethoxycarbonylmethyl, 3-bromopropoxycarbonylmethyl, 4-chlorobutoxycarbonylmethyl, (1-fluoromethyl-2-fluoroethoxycarbonyl)methyl, 1-(2-fluoroethoxycarbonyl)ethyl, 1-(2,2,2-trifluoroethoxycarbonyl)ethyl, 1-(3-bromopropoxycarbonyl)ethyl, 1-(4-chlorobutoxycarbonyl)ethyl, 1-(1-fluoromethyl-2-fluoroethoxycarbonyl)ethyl, etc.;

$C_1$–$C_{10}$ alkoxycarbonyl $C_1$–$C_5$ haloalkyl includes methoxycarbonylchloromethyl, ethoxycarbonylchloromethyl, propoxycarbonylchloromethyl, isopropoxycarbonylchloromethyl, etc.;

$C_1$–$C_{10}$ haloalkoxycarbonyl $C_1$–$C_5$ haloalkyl includes 2-fluoroethoxycarbonylchloromethyl, 2,2,2-trifluoroeethoxycarbonylchloromethyl, 3-bromopropoxycarbonylchloromethyl, 4-chlorobutoxycarbonylchloromethyl, etc.;

$C_3$–$C_{10}$ cycloalkoxycarbonyl $C_1$–$C_5$ alkyl includes cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, 1-cyclohexyloxycarbonylethyl, etc.;

$C_3$–$C_{10}$ halocycloalkoxycarbonyl $C_1$–$C_5$ alkyl includes 3-chlorocyclohexyloxycarbonylmethyl, 3-bromocyclohexyloxycarbonylmethyl, 3-fluorocyclohexyloxycarbonylmethyl, 1-(3-chlorocyclohexyloxycarbonyl)ethyl, 1-(3-bromocyclohexyloxycarbonyl)ethyl, 1-(3-fluorocyclohexyloxycarbonyl)ethyl, etc.;

$C_3$–$C_{10}$ halocycloalkoxycarbonyl $C_1$–$C_5$ haloalkyl includes 3-chlorocyclohexyloxycarbonylchloromethyl, 3-bromocyclohexyloxycarbonylchloromethyl, 3-fluorocyclohexyloxycarbonylchloromethyl, etc.;

$C_3$–$C_{10}$ cycloalkoxycarbonyl $C_1$–$C_5$ haloalkyl includes cyclobutyloxycarbonylchloromethyl, cyclopentyloxycarbonylchloromethyl, cyclohexyloxycarbonylchloromethyl, etc.;

$C_1$–$C_6$ alkoxy $C_1$–$C_6$ alkyl includes methoxyethyl, 1-methoxyethyl, ethoxymethyl, etc.;

$C_1$–$C_6$ alkoxy $C_1$–$C_6$ haloalkyl includes methoxychloromethyl, etc.;

$C_1$–$C_6$ haloalkoxy $C_1$–$C_6$ alkyl includes 2,2,2-trifluoroethoxymethyl, etc.;

$C_1$–$C_6$ haloalkoxy $C_1$–$C_6$ haloalkyl includes chloromethoxychloromethyl, etc.;

$C_1$–$C_6$ alkylthio $C_1$–$C_6$ alkyl includes methylthiomethyl, 1-methylthioethyl, ethylthiomethyl, etc.;

$C_1$–$C_6$ alkylthio $C_1$–$C_6$ haloalkyl includes methylthiochloromethyl, etc.;

$C_1$–$C_6$ haloalkylthio $C_1$–$C_6$ alkyl includes 2,2,2-trifluoroethylthiomethyl, etc.;

$C_1$–$C_6$ haloalkylthio $C_1$–$C_6$ haloalkyl includes chloromethylthiochloromethyl, etc.;

cyano $C_1$–$C_4$ alkyl includes cyanomethyl cyanoethyl, 1-methylcyanoethyl, etc.;

aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

aryl $C_1$–$C_3$ alkyl that may have substituent(s) includes benzyl, phenethyl, 1-methylbenzyl, 2-chlorobenzyl, 3-chlorobenzyl, 4-chlorobenzyl, 2-methoxybenzyl, 3-methoxybenzyl, 4-methoxybenzyl, etc.; and arylcarbonyl that may have substituent(s) includes benzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 2,6-dichlorobenzoyl, 3,4-dichlorobenzoyl, etc.;

in the definition of $R^9$, $C_1$–$C_{10}$ alkyl includes methyl, ethyl, isopropyl, n-butyl, isopentyl, n-octyl, etc.;

$C_1$–$C_{10}$ haloalkyl includes 2-fluoroethyl, 2,2,2-trifluoroethyl, 5-chloro-n-pentyl, 7-bromoheptyl, etc.;

$C_3$–$C_8$ alkenyl includes allyl, 1-methyl-2-propenyl, 3-butenyl, 2-butenyl, 3-methyl-2-butenyl, 2-methyl-3-butenyl, etc.;

$C_3$–$C_8$ haloalkenyl includes 2-chloro-2-propenyl, 3,3-dichloro-2-propenyl, etc.;

$C_3$–$C_8$ alkynyl includes propargyl, 1-methyl-2-propynyl, 2-butynyl, 3-butynyl, 1,1-dimethyl-2-propynyl, etc.;

$C_3$–$C_8$ haloalkynyl includes 3-iodo-2-propynyl, 3-bromo-2-propynyl, etc.;

$C_3$–$C_{10}$ cycloalkyl includes cyclopropyl, cyclopentyl, cyclohexyl, 4,4-dimethylcyclohexyl, etc.;

$C_3$–$C_{10}$ halocycloalkyl includes 2-fluorocyclopentyl, 3,4-dichlorocyclohexyl, etc.;

$C_3$–$C_{10}$ cycloalkenyl includes 2-cyclohexenyl, 3-cyclohexenyl, etc.;

$C_3$–$C_{10}$ halocycloalkenyl includes 4-chloro-2-cyclohexenyl, etc.;

$C_1$–$C_5$ alkylcarbonyl includes acetyl, propionyl, etc.;

$C_1$–$C_5$ haloalkylcarbonyl includes trifluoroacetyl, dichloroacetyl, pentafluoropropionyl, etc.;

$C_3$–$C_6$ cycloalkylcarbonyl includes cyclopropylcarbonyl, cyclopentylcarbonyl, etc.;

$C_3$–$C_6$ halocycloalkylcarbonyl includes 2,2-difluorocyclopentylcarbonyl, etc.;

$C_1$–$C_6$ alkylcarbonyl $C_1$–$C_6$ alkyl includes 2-oxopropyl, 4-oxopentyl, 3-ethyl-2-oxooctyl, 5-methyl-4-oxohexyl, etc.;

$C_1$–$C_6$ haloalkylcarbonyl $C_1$–$C_6$ alkyl includes 3,3,3-trifluoro-2-oxopropyl, etc.;

$C_1$–$C_6$ alkylcarbonyl $C_1$–$C_6$ haloalkyl includes 1-chloro-2-oxopropyl, etc.;

$C_1$–$C_6$ haloalkylcarbonyl $C_1$–$C_6$ haloalkyl includes 2,7-difluoro-4-oxoheptyl, etc.;

$C_1$–$C_6$ alkoxycarbonyl includes methoxycarbonyl, ethoxycarbonyl, propoxycarbonyl, butoxycarbonyl, amyloxycarbonyl, isopropoxycarbonyl, isobutoxycarbonyl, isoamyloxycarbonyl, etc.;

$C_1$–$C_6$ haloalkoxycarbonyl includes 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dichloroethoxycarbonyl, 2,2,2-trifluoroethoxycarbonyl, 2,2,2-trichloroethoxycarbonyl, 2,2,2-tribromoethoxycarbonyl, etc.;

$C_3$–$C_{10}$ cycloalkoxycarbonyl includes cyclobutyloxycarbonyl, cyclopentyloxycarbonyl, cyclohexyloxycarbonyl, etc.;

carboxy $C_1$–$C_5$ alkyl includes carboxymethyl, 1-carboxyethyl, 1-carboxy-1-methylethyl, etc.;

$C_1$–$C_{10}$ alkoxycarbonyl $C_1$–$C_5$ alkyl includes methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, etc.;

$C_1$–$C_{10}$ haloalkoxycarbonyl $C_1$–$C_5$ alkyl includes 2-fluoroethoxycarbonylmethyl, 2,2,2-trifluoroethoxycarbonylmethyl, 3-bromopropoxycarbonylmethyl, 4-chlorobutoxycarbonylmethyl, (1-fluoromethyl-2-fluoroethoxycarbonyl)methyl, 1-(2-fluoroethoxycarbonyl)ethyl, 1-(2,2,2-trifluoroethoxycarbonyl)ethyl, 1-(3-bromopropoxycarbonyl)ethyl, 1-(4-chlorobutoxycarbonyl)ethyl, 1-(1-fluoromethyl-2-fluoroethoxycarbonyl)ethyl, etc.;

$C_1$–$C_{10}$ alkoxycarbonyl $C_1$–$C_5$ haloalkyl includes methoxycarbonylchloromethyl, ethoxycarbonylchloromethyl, propoxycarbonylchloromethyl, isopropoxycarbonylchloromethyl, etc.;

$C_1$–$C_{10}$ haloalkoxycarbonyl $C_1$–$C_5$ haloalkyl includes 2-fluoroethoxycarbonylchloromethyl, 2,2,2-trifluoroethoxycarbonylchloromethyl, 3-bromopropoxycarbonylchloromethyl, 4-chlorobutoxycarbonylchloromethyl, etc.;

$C_3$–$C_{10}$ cycloalkoxycarbonyl $C_1$–$C_5$ alkyl includes cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, 1-cyclohexyloxycarbonylethyl, etc.;

$C_3$–$C_{10}$ halocycloalkoxycarbonyl $C_1$–$C_5$ alkyl includes 3-chlorocyclohexyloxycarbonylmethyl, 3-bromocyclohexyloxycarbonylmethyl, 3-fluorocyclohexyloxycarbonylmethyl, 1-(3-chlorocyclohexyloxycarbonyl)ethyl, 1-(3-bromocyclohexyloxycarbonyl)ethyl, 1-(3-fluorocyclohexyloxycarbonyl)ethyl, etc.;

$C_3$–$C_{10}$ halocycloalkoxycarbonyl $C_1$–$C_5$ haloalkyl includes 3-chlorocyclohexyloxycarbonylchloromethyl, 3-bromocyclohexyloxycarbonylchloromethyl, 3-fluorocyclohexyloxycarbonylchloromethyl, etc.;

$C_3$–$C_{10}$ cycloalkoxycarbonyl $C_1$–$C_5$ haloalkyl includes cyclobutyloxycarbonylchloromethyl, cyclopentyloxycarbonylchloromethyl, cyclohexyloxycarbonylchloromethyl, etc.;

$C_1$–$C_6$ alkoxy $C_1$–$C_6$ alkyl includes a methoxymethyl, 1-methoxyethyl, ethoxymethyl, etc.;

$C_1$–$C_6$ alkoxy $C_1$–$C_6$ haloalkyl includes methoxychloromethyl, etc.;

$C_1$–$C_6$ haloalkoxy $C_1$–$C_6$ alkyl includes 2,2,2-trifuoroethoxymethyl, etc.;

$C_1$–$C_6$ haloalkoxy $C_1$–$C_6$ haloalkyl includes chloromethoxychloromethyl, etc.;

$C_1$–$C_6$ alkylthio $C_1$–$C_6$ alkyl includes methylthiomethyl, 1-methylthioethyl, ethylthiomethyl, etc.;

$C_1$–$C_6$ alkylthio $C_1$–$C_6$ haloalkyl includes methylthiochloromethyl, etc.;

$C_1$–$C_6$ haloalkylthio $C_1$–$C_6$ alkyl includes 2,2,2-trifluoroethylthiomethyl, etc.;

$C_1$–$C_6$ haloalkylthio $C_1$–$C_6$ haloalkyl includes chloromethylthiochloromethyl, etc.; cyano $C_1$–$C_4$ alkyl includes cyanomethyl, cyanoethyl, 1-methyl-1-cyanoethyl, etc.; aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

aryl $C_1$–$C_3$ alkyl that may have substituent(s) includes benzyl, phenethyl, 1-methylbenzyl, 2-chlorobenzyl, 3-chlorobenzyl, 4-chlorobenzyl, 2-methoxybenzyl, 3-methoxybenzyl, 4-methoxybenzyl, etc.; and arylcarbonyl that may have substituent(s) includes benzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 2,6-dichlorobenzoyl, 3,4-dichlorobenzoyl, etc.;

in the definition of $R^{10}$, $C_1$–$C_{10}$ alkyl includes methyl, ethyl, isopropyl, n-butyl, isopentyl, n-octyl, etc.;

$C_1$–$C_{10}$ haloalkyl includes 2-fluoroethyl, 2,2,2-triflouroethyl, 5-chloro-n-pentyl, 7-bromoheptyl, etc.;

$C_3$–$C_8$ alkenyl includes allyl, 1-methyl-2-propenyl, 3-butenyl, 2-butenyl, 3-methyl-2-butenyl, 2-methyl-3-butenyl, etc.;

$C_3$–$C_8$ haloalkenyl includes 2-chloro-2-propenyl, 3,3-dichloro-2-propenyl, etc.;

$C_3$–$C_8$ alkynyl includes propargyl, 1-methyl-2-propynyl, 2-butynyl, 3-butynyl, 1,1-dimethyl-2-propynyl, etc.;

$C_3$–$C_8$ haloalkynyl includes 3-iodo-2-propynyl, 3-bromo-2-propynyl, etc.;

$C_3$–$C_{10}$ cycloalkyl includes cyclopropyl, cyclopentyl, cyclohexyl, 4,4-dimethylcyclohexyl, etc.;

$C_3$–$C_{10}$ halocycloalkyl includes 2-fluorocyclopentyl, 3,4-dichlorocyclohexyl, etc.;

$C_3$–$C_{10}$ cycloalkenyl includes 2-cyclohexenyl, 3-cyclohexenyl, etc.;

$C_3$–$C_{10}$ halocycloalkenyl includes 4-chloro-2-cyclohexenyl, etc.;

$C_1$–$C_5$ alkylcarbonyl includes acetyl, propionyl, etc.;

$C_1$–$C_5$ haloalkylcarbonyl includes trifluoroacetyl, dichloroacetyl, pentafluoropropionyl, etc.;

$C_3$–$C_6$ cycloalkylcarbonyl includes cyclopropylcarbonyl, cyclopentylcarbonyl, etc.;

$C_3$–$C_6$ halocycloalkylcarbonyl includes 2,2-difluorocyclopentylcarbonyl, etc.;

$C_1$–$C_6$ alkylcarbonyl $C_1$–$C_6$ alkyl includes 2-oxopropyl, 4-oxopentyl, 3-ethyl-2-oxooctyl, 5-methyl-4-oxohexyl, etc.;

$C_1$–$C_6$ haloalkylcarbonyl $C_1$–$C_6$ alkyl includes 3,3,3-trifluoro-2-oxopropyl, etc.;

$C_1$–$C_6$ alkylcarbonyl $C_1$–$C_6$ haloalkyl includes 1-chloro-3.3.3-trifluoro-2-oxopropyl, etc.;

$C_1$–$C_6$ haloalkylcarbonyl $C_1$–$C_6$ haloalkyl includes 2,7-difluoro-4-oxoheptyl, etc.;

$C_1$–$C_6$ alkoxycarbonyl includes methoxycarbonyl, ethoxycarbonyl, propoxycarbonyl, butoxycarbonyl, amyloxycarbonyl, isopropoxycarbonyl, isobutoxycarbonyl, isoamyloxycarbonyl, etc.;

$C_1$–$C_6$ haloalkoxycarbonyl includes 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dichloroethoxycarbonyl, 2,2,2-trifluoroethoxycarbonyl, 2,2,2-trichloroethoxycarbonyl or 2,2,2-tribromoethoxycarbonyl, etc.;

$C_3$–$C_{10}$ cycloalkoxycarbonyl includes cyclobutyloxycarbonyl, cyclopentyloxycarbonyl, cyclohexyloxycarbonyl, etc.;

carboxy $C_1$–$C_5$ alkyl includes carboxymethyl, 1-carboxyethyl, 1-carboxy-1-methylethyl, etc.;

$C_1$–$C_{10}$ alkoxycarbonyl $C_1$–$C_5$ alkyl includes methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, etc.;

$C_1$–$C_{10}$ haloalkoxycarbonyl $C_1$–$C_5$ alkyl includes 2-fluoroethoxycarbonylmethyl, 2,2,2-trifluoroethoxycarbonylmethyl, 3-bromopropoxycarbonylmethyl, 4-chlorobutoxycarbonylmethyl, (1-fluoromethyl-2-fluoroethoxycarbony)methyl, 1-(2-fluoroethoxycarbonyl)ethyl, 1-(2,2,2-trifluoroethoxycarbonyl)ethyl, 1-(3-bromopropoxycarbonyl)ethyl, 1-(4-chlorobutoxycarbonyl)ethyl, 1-(1-fluoromethyl-2-fluoroethoxycarbonyl)ethyl, etc.;

$C_1$–$C_{10}$ alkoxycarbonyl $C_1$–$C_5$ haloalkyl includes methoxycarbonylchloromethyl, ethoxycarbonylchloromethyl, propoxycarbonylchloromethyl, isopropoxycarbonylchloromethyl, etc.;

$C_1$–$C_{10}$ haloalkoxycarbonyl $C_1$–$C_5$ haloalkyl includes 2-fluoroethoxycarbonylchloromethyl, 2,2,2-trifluoroethoxycarbonylchloromethyl, 3-bromopropoxycarbonylchloromethyl, 4-chlorobutoxycarbonylchloromethyl, etc.;

$C_3$–$C_{10}$ cycloalkoxycarbonyl $C_1$–$C_5$ alkyl includes cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, 1-cyclohexyloxycarbonylethyl, etc.;

$C_3$–$C_{10}$ halocycloalkoxycarbonyl $C_1$–$C_5$ alkyl includes 3-chlorocyclohexyloxycarbonylmethyl, 3-bromocyclohexyloxycarbonylmethyl, 3-fluorocyclohexyloxycarbonylmethyl, 1-(3-chlorocyclohexyloxycarbonyl)ethyl, 1-(3-bromocyclohexyloxycarbonyl)ethyl, 1-(3-fluorocyclohexyloxycarbonyl)ethyl, etc.;

$C_3$–$C_{10}$ halocycloalkoxycarbonyl $C_1$–$C_5$ haloalkyl includes 3-chlorocyclohexyloxycarbonylchloromethyl, 3-bromocyclohexyloxycarbonylchloromethyl, 3-fluorocyclohexyloxycarbonylchloromethyl, etc.;

$C_3$–$C_{10}$ cycloalkoxycarbonyl $C_1$–$C_5$ haloalkyl includes cyclobutyloxycarbonylchloromethyl, cyclopentyloxycarbonylchloromethyl, cyclohexyloxycarbonylchloromethyl, etc.;

$C_1$–$C_6$ alkoxy $C_1$–$C_6$ alkyl includes methoxymethyl, 1-methoxyethyl, ethoxymethyl, etc.;

$C_1$–$C_6$ alkoxy $C_1$–$C_6$ haloalkyl includes methoxychloromethyl, etc.;

$C_1$–$C_6$ haloalkoxy $C_1$–$C_6$ alkyl includes 2,2,2-trifluoroethoxymethyl, etc.;

$C_1$–$C_6$ haloalkoxy $C_1$–$C_6$ haloalkyl includes chloromethoxychloromethyl, etc.;

$C_1$–$C_6$ alkylthio $C_1$–$C_6$ alkyl includes methylthiomethyl, 1-methylthioethyl, ethylthiomethyl, etc.;

$C_1$–$C_6$ alkylthio $C_1$–$C_6$ haloalkyl includes methylthiochloromethyl, etc.;

$C_1$–$C_6$ haloalkylthio $C_1$–$C_6$ alkyl includes (2,2,2-trifluoroethylthio)methyl, etc.;

$C_1$–$C_6$ haloalkylthio $C_1$–$C_6$ haloalkyl includes chloromethylthiochloromethyl, etc.; cyano $C_1$–$C_4$ alkyl includes cyanomethyl, cyanoethyl, 1-methyl-1-cyanoethyl, etc.; aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

aryl $C_1$–$C_3$ alkyl that may have substituent(s) includes benzyl, phenethyl, 1-methylbenzyl, 2-chlorobenzyl, 3-chlorobenzyl, 4-chlorobenzyl, 2-methoxybenzyl, 3-methoxybenzyl, 4-methoxybenzyl, etc.; and arylcarbonyl that may have substituent(s) includes benzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 2,6-dichlorobenzoyl, 3,4-dichlorobenzoyl, etc.;

in the definition of $R^{11}$, $C_1$–$C_{10}$ alkyl includes methyl, ethyl, isopropyl, n-butyl, t-butyl, isopentyl, n-hexyl, n-octyl, etc.;

$C_1$–$C_{10}$ haloalkyl includes 2-fluoroethyl, 2,2,2-triflouroethyl, 5-chloro-n-pentyl, 7-bromoheptyl, etc.;

$C_3$–$C_8$ cycloalkyl includes cyclopropyl, cyclopentyl, cyclohexyl, 4,4-dimethylcyclohexyl, etc.;

$C_3$–$C_8$ cyclohaloalkyl includes 2-fluorocyclopentyl, 3,4-dichlorocyclohexyl, etc.; and carboxy $C_1$–$C_3$ alkyl includes carboxymethyl, 1-carboxyethyl, 1-carboxy-1-methylethyl, etc.;

$C_1$–$C_5$ alkoxycarbonyl $C_1$–$C_3$ alkyl includes methoxycarbonylmethyl, ethoxycabonylmethyl, 1-ethoxycarbonylethyl, 1-ethoxycarbonyl-1-methylethyl, etc.;

$C_1$–$C_5$ haloalkoxycarbonyl $C_1$–$C_3$ alkyl includes 2-fluoroethoxycarbonylmethyl, 2,2,2-trifluoroethoxycarbonylmethyl, 3-bromopropoxycarbonylmethyl, 4-chlorobutoxycarbonylmethyl, (1-fluoromethyl-2-fluoroethoxycarbonyl)methyl, etc.;

$C_3$–$C_6$ cycloalkoxycarbonyl $C_1$–$C_3$ alkyl includes cyclopropyloxycarbonylmethyl, 1-cyclopropyloxycarbonylethyl, 1-cyclopropyloxycarbonyl-1-methylethyl, etc.;

$C_3$–$C_8$ alkenyloxycarbonyl $C_1$–$C_3$ alkyl includes allyloxycarbonylmethyl, 1-allyloxycarbonylethyl, 1-allyloxycarbonyl-1-methylethyl, etc.;

in the definition of $R^{12}$, $C_1$–$C_5$ alkyl includes methyl, ethyl, n-propyl, isopropyl, etc.

$C_1$–$C_5$ haloalkyl includes chloromethyl, bromomethyl, trifluoromethyl, chlorodifluormethyl, difluoromethyl, pentafluoromethyl, etc.;

$C_3$–$C_6$ cycloalkyl includes cyclopropyl, cyclopentyl, 1-methylcyclopropyl, etc.; and $C_3$–$C_6$ halocycloalkyl includes 2,2-difluorocyclopropyl, 3-chlorocyclopentyl, etc.;

in the definition of $R^{13}$, $C_1$–$C_{10}$ alkyl includes methyl, ethyl, n-propyl, isopropyl, n-butyl, t-butyl, n-pentyl, n-hexyl, etc.; and $C_1$–$C_{10}$ haloalkyl includes chloromethyl, chloroethyl, 2,2,2-triflouroethyl, etc.;

in the definition of $R^{14}$, halogen means fluorine, chlorine or bromoine; and $C_1$–$C_3$ alkyl includes methyl, ethyl, etc.;

in the definition of $R^{16}$, halogen means fluorine, chlorine or bromoine;

$C_1$–$C_4$ alkyl includes methyl, ethyl, isopropyl, etc.;

$C_1$–$C_4$ haloalkyl includes chloromethyl, 2-chloroethyl, trifluoromethyl, tetrafluoroethyl, chlorodifluoromethyl, etc.;

$C_3$–$C_5$ cycloalkyl includes cyclopropyl, cyclopentyl,1-methylcyclopropyl, etc.; and $C_3$–$C_5$ halocycloalkyl includes 2,2-difluorocyclopropyl, 3-chlorocyclopentyl, etc.;

in the definition of $R^{17}$, $C_1$–$C_{10}$ alkyl includes methyl, ethyl, n-propyl, isopropyl, n-butyl, t-butyl, n-pentyl, n-hexyl, etc.;

$C_1$–$C_{10}$ haloalkyl includes chloroethyl or 2,2,2-trifluoroethyl, etc.;

$C_3$–$C_6$ cycloalkyl includes cyclopropyl, cyclopentyl, cyclohexyl, 1-methylcyclopropyl, etc.;

$C_3$–$C_6$ halocycloalkyl includes 2,2-difluorocyclopropyl, 3-chlorocyclopentyl, etc.;

$C_3$–$C_5$ alkenyl includes allyl, 1-methyl-2-propenyl, 3-butenyl, 2-butenyl, 3-methyl-2-butenyl, 2-methyl-3-butenyl, etc.;

$C_3$–$C_5$ haloalkenyl includes 2-chloro-2-propenyl, 3,3-dichloro-2-propenyl, etc.;

$C_3$–$C_5$ alkynyl includes propargyl, 1-methyl-2-propynyl, 2-butynyl, 3-butynyl, 1,1-dimethyl-2-propynyl, etc.;

$C_3$–$C_5$ haloalkynyl includes 3-iodo-2-propynyl, 3-bromo-2-propynyl, etc.;

carboxy $C_1$–$C_3$ alkyl includes carboxymethyl, 1-carboxyethyl, 1-carboxy-1-methylethyl, etc.;

$C_1$–$C_5$ alkoxycarbonyl $C_1$–$C_3$ alkyl includes methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, etc.;

aryl that may have substituent(s) includes phenyl, 2-chlorophenyl, 2-nitrophenyl, 2-trifluorophenyl, 2-methoxyphenyl, 4-chlorophenyl, 4-nitrophenyl, 4-isopropoxyphenyl, 4-fluorophenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

aryl $C_1$–$C_3$ alkyl that may have substituent(s) includes benzyl, phenethyl, 1-methylbenzyl, 2-chlorobenzyl, 3-chlorobenzyl, 4-chlorobenzyl, 2-methoxybenzyl, 3-methoxybenzyl, 4-methoxybenzyl, etc.;

arylcarbonyl that may have substituent(s) includes benzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 2,6-dichlorobenzoyl, 3,4-dichlorobenzoyl, etc.; and in the definition of $R^{18}$, $C_1$–$C_{10}$ alkyl includes methyl, ethyl, isopropyl, n-butyl, isopentyl, n-octyl, etc.;

$C_1$–$C_{10}$ haloalkyl includes 2-fluoroethyl, 2,2,2-trifluoroethyl, 5-chloro-n-pentyl, 7-bromoheptyl, etc.; and aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

in the definition of $R^{19}$, $C_1$–$C_{10}$ alkyl includes methyl, ethyl, isopropyl, n-butyl, isopentyl, n-octyl, etc.;

$C_1$–$C_{10}$ haloalkyl includes 2-fluoroethyl, 2,2,2-trifluoroethyl, 5-chloro-n-pentyl, 7-bromoheptyl, etc.;

$C_3$–$C_8$ cycloalkyl includes cyclopropyl, cyclopentyl, cyclohexyl, 1-methylcyclopropyl, 4,4-dimethylcyclohexyl, etc.;

$C_3$–$C_8$ halocycloalkyl includes 2,2-difluorocyclopropyl, 3-chlorocyclopentyl, 4,4-difluorocyclohexyl, etc.; and aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

in the definition of $R^{20}$, $C_1$–$C_{10}$ alkyl includes methyl, ethyl, isopropyl, n-butyl, isopentyl, n-octyl, etc.;

$C_1$–$C_{10}$ haloalkyl includes chloromethyl, trichloromethyl, trifluoromethyl, 2-chloroethyl, 2-fluoroethyl, 3-chloropropyl, 2,2,2-trifluoroethyl, 5-chloro-n-pentyl, 7-bromoheptyl, etc.;

$C_3$–$C_8$ cycloalkyl includes cyclopropyl, cyclopentyl, cyclohexyl, 1-methylcyclopropyl, 4,4-dimethylcyclohexyl, etc.;

$C_3$–$C_8$ halocycloalkyl includes 2,2-difluorocyclopropyl, 3-chlorocyclopentyl, 4,4-difluorocyclohexyl, etc.; and aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, etc.;

in the definition of $R^{21}$, $C_1$–$C_5$ alkyl includes methyl, ethyl, n-propyl, isopropyl, etc.;

in the definition of $R^{22}$, $C_1$–$C_5$ alkyl includes methyl, ethyl, n-propyl, isopropyl, etc.; $C_1$–$C_5$ haloalkyl includes 2-chloroethyl, tetrafluoroethyl, fluoroethyl, 3-chloro-n-propyl, 2-chloro-2-methylpropyl, etc.; and aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, 3,4-dimethylphenyl, 2,4-dimethylphenyl, 2,5-dimethylphenyl, etc.;

in the definition of $R^{23}$, $C_1$–$C_{10}$ alkyl includes methyl, ethyl, isopropyl, n-butyl, isopentyl, n-octyl, 4,4-dimethyl-n-hexyl, etc.;

$C_1$–$C_{10}$ haloalkyl includes 2-fluoroethyl, 2-chloroethyl, 3-chloro-n-propyl, 2,2,2-trifluoroethyl, 5-chloro-n-pentyl, 7-bromoheptyl, etc.;

$C_3$–$C_{10}$ cycloalkyl includes cyclopropyl, cyclopentyl, cyclohexyl, 1-methylcyclopropyl, 4,4-dimethylcyclohexyl, 2,2,4,4-tetramethylcyclohexyl, etc.;

$C_3$–$C_{10}$ halocycloalkyl includes 2,2-difluorocyclopropyl, 3-chlorocyclopentyl, 4,4-difluorocyclohexyl, etc.; and aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, 3,4-dimethylphenyl, 2,4-dimethylphenyl, 2,5 dimethylphenyl, etc.;

in the definition of $R^{24}$, $C_1$–$C_{10}$ alkyl includes methyl, ethyl, isopropyl, n-butyl, t-butyl, n-pentyl, isopentyl, n-octyl, 4,4-dimethyl-n-hexyl, etc.; and $C_1$–$C_{10}$ haloalkyl includes 2-fluoroethyl, 2-chloroethyl, 3-chloro-n-propyl, 2,2,2-trifluoroethyl, 5-chloro-n-pentyl, 7-bromoheptyl, etc.;

in the definition of $R^{25}$, $C_1$–$C_5$ alkyl includes methyl, ethyl, isopropyl, n-butyl, t-butyl, n-pentyl, isopentyl, etc.; and $C_1$–$C_5$ haloalkyl includes 2-fluoroethyl, 2-chloroethyl, 3-chloro-n-propyl, 2,2,2-trifluoroethyl, 5-chloro-n-pentyl, etc.;

in the definition of $R^{26}$, $C_1$–$C_{10}$ alkyl includes methyl, ethyl, isopropyl, n-butyl, t-butyl, n-pentyl, isopentyl, n-octyl, 4,4-dimethyl-n-hexyl, etc.; and $C_1-C_{10}$ haloalkyl includes 2-fluoroethyl, 2-chloroethyl, 3-chloro-n-propyl, 2,2,2-trifluoroethyl, 5-chloro-n-pentyl, 2-chloro-1,1,4,4-tetramethylhexyl, etc.;

in the definition of $R^{27}$, $C_1-C_{10}$ alkyl includes methyl, ethyl, isopropyl, n-butyl, isobutyl, t-butyl, n-pentyl, isopentyl, n-hexyl, n-octyl, etc.;

in the definition of $R^{28}$, $C_1-C_{10}$ alkyl includes methyl, ethyl, isopropyl, n-butyl, isobutyl, t-butyl n-pentyl, isopentyl, n-hexyl, n-octyl, etc.;

$C_1-C_{10}$ haloalkyl includes 2-fluoroethyl, 2-chloroethyl, 3-chloro-n-propyl, 2,2,2-trifluoroethyl, 5-chloro-n-pentyl, etc.;

$C_3-C_{10}$ cycloalkyl includes cyclopropyl, cyclopentyl, cyclohexyl, 1-methylcyclopropyl, 4,4-dimethylcyclohexyl, 2,2,4,4-tetramethylcyclohexyl, etc.;

$C_3-C_{10}$ halocycloalkyl includes 2,2-difluorocyclopropyl, 3-chlorocyclopentyl, 4,4-difluorocyclohexyl, etc.; and aryl that may have substituent(s) includes phenyl, 2-chlorophenyl, 2-nitrophenyl, 2-trifluoromethylphenyl, 2-methoxyphenyl, 4-chlorophenyl, 4-nitrophenyl, 4-isopropoxyphenyl, 4-fluorophenyl, 4-methylphenyl, 4-trifluoromethylphenyl, 3-nitrophenyl, 3-methoxyphenyl, 3-methylphenyl, 3-trifluoromethylphenyl, 3-bromophenyl, 3-methoxycarbonylphenyl, 3-trifluoromethoxyphenyl, 3,4-dichlorophenyl, 2,4-dichlorophenyl, 2,5-dichlorophenyl, 3,4-dimethylphenyl, 2,4-dimethylphenyl, 2,5-dimethylphenyl, etc.; and in the definition of $E^1, E^2, E^3, E^4, E^5, E^6, E^7, E^8, E^9, E^{10}, E^{11}, E^{11}, E^{12}, E^{13}$ and $E^{14}$ halogen means fluorine, chlorine, bromine or iodine; and $C_1-C_3$ alkyl includes methyl, ethyl, propyl, isopropyl.

Among the present compounds, preferred are 8-(2,3-dichloro-5-isopropyloxybenzyl)-5-(trifluoromethyl)-2,3,7,8-tetrahydoimidazo[1,2-a]pyrimidin-7-s one and 8-(2,3-dichloro-5-isopropyloxybenzyl)-5-(trifluoromethyl)-7,8-dihydoimidazo[1,2-a]pyrimidin-7-one.

Moreover, for the present invention compound, there are situations when double bonds educe geometric isomers or when asymmetric carbons educe optical isomers and diastereoisomers. As such, the present inventive compounds also comprise isomers thereof and mixture of such isomers.

The present invention compound can be produced by utilizing a production method or methods, such as are set forth below.

Production Method 1

A production method that follows the scheme of Chemical Formula 5 below.

[Chemical Formula 5]

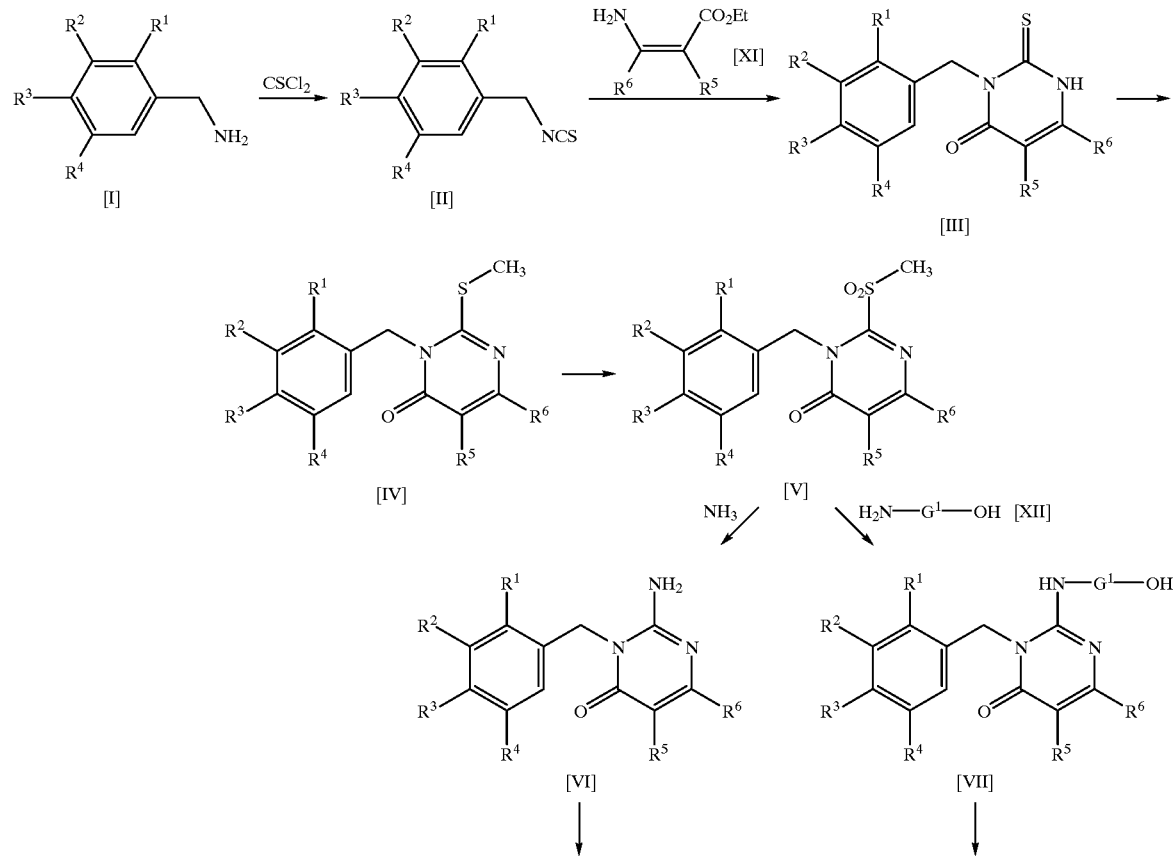

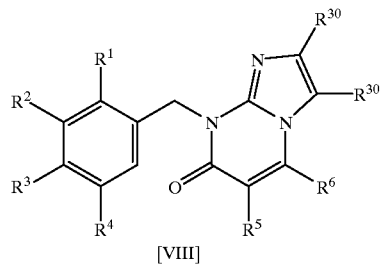
[VIII]

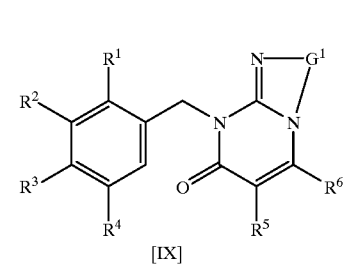
[IX]

[Wherein, $R^1$, $R^2$, $R^3$, $R^4$, $R^5$, and $R^6$ represent the same definitions as mentioned above and $R^{30}$ represents hydrogen or $C_1$–$C_3$ alkyl. $G^1$ represents —C($E^{101}$)$E^{102}$—C($E^{103}$)$E^{104}$—, or —C($E^{105}$)$E^{106}$—C($E^{107}$)$E^{108}$—C($E^{109}$)$E^{110}$— (wherein $E^{101}$, $E^{102}$, $E^{103}$, $E^{104}$, $E^{105}$, $E^{106}$, $E^{107}$, $E^{108}$, $E^{109}$ and $E^{110}$, same or different, each represents hydrogen or $C_1$–$C_3$ alkyl)]

The reaction of each step in the above reaction scheme, for example, may be performed by utilizing the methods below.

1) The Method to Produce Compound [II] from Compound [I]

Compound [II] may be produced by reacting compound [1] and thiophosgene within a solvent. Solvents utilized for the reaction include, aliphatic hydrocarbons such as hexane, heptane, ligroin, cyclohexane and petroleum ether; aromatic hydrocarbons such as benzene, toluene and xylene; halogenated hydrocarbons such as chlorobenzene and dichlorobenzene; ethers such as diethyl ether, diisopropyl ether, dioxane, THF and ethylene glycol dimethyl ether; nitro compounds such as nitrobenzene; acid amides such as N,N-dimethylformamide; and mixtures thereof. The reaction temperature is usually within the limits of room temperature to the solvent reflux temperature, and the reaction time is usually within the limits of a moment (several seconds) to 72 hours.

After the completion of the reaction, the reaction mixture is subjected to ordinary post-treatment such as concentration, if necessary, and may be purified by the procedure such as chromatography and recrystallization. Thus the objective material can be isolated.

2) A Method to Produce Compound [III] from Compound [II]

Compound [III] can be produced by reacting compound [II] and compound [XI] within a solvent, and in the presence of a base.

| | |
|---|---|
| amount of compound [XI]: | based on 1 mole of compound [II], 1 mole to an excess amount |
| solvent: | dimethylformamide or the like |
| temperature: | −20° C. to 100° C. |
| time: | a moment (several seconds) to 72 hours |
| base: | inorganic bases such as sodium hydride |
| amount of base: | based on 1 mole of compound [II], 1 mole to an excess amount |

After the completion of the reaction, diluted hydrochloric acid is added to the reaction mixture to collect the precipitated crystals by filtration or the reaction mixture is subjected to ordinary post-treatment such as extraction with an organic solvent and concentration. If necessary, a purification procedure such as chromatography and recrystallization may be performed. Thus the objective material can be obtained.

3) The Method to Produce Compound [IV] from Compound [III]

Compound [IV] may be produced by reacting compound [III] and a methylating agent within a solvent, and in the presence of a base.

| | |
|---|---|
| amount of methylating agent: | based on 1 mole of compound [III], 1 mole to an excess amount |
| Sort of methylating agent | iodomethane, dimethyl sulfate, or the like |
| solvent: | dimethylformamide |
| temperature: | −10° C. to 100° C. |
| time: | a moment (several seconds) to 24 hours |
| base: | organic bases such as triethylamine or inorganic bases such as potassium carbonate |
| amount of base: | based on 1 mole of compound [III], 1 mole to an excess amount |

After the completion of the reaction, diluted hydrochloric acid is added to the reaction mixture to collect the precipitated crystals by filtration, or the reaction mixture is subjected to ordinary post-treatment such as extraction with an organic solvent and concentration. If necessary, the purification procedure such as chromatography and recrystallization may be performed. Thus the objective material can be obtained.

4) The Method to Produce Compound [V] from Compound [IV]

Compound [V] may be produced by reacting compound [IV] and an oxidation agent within a solvent.

| | |
|---|---|
| amount of oxidation agent: | based on 1 mole of compound [IV], 2 moles to an excess amount |
| sort of oxidation agent: | m-chloro perbenzoic acid |
| solvent: | chloroform |
| temperature: | −10° C. to temperature to reflux |
| time: | a moment (several seconds) to 48 hours |

After the completion of the reaction, the reaction mixture is washed by the solution of sodium sulfite, etc. and then subjected to ordinary post-treatment such as extraction with an organic solvent and concentration. If necessary, a purification procedure such as chromatography and recrystallization may be performed. Thus the objective material can be obtained.

5) The Method to Produce Compound [VI] from Compound [V]

Compound [VI] may be produced by reacting compound [V] and ammonia within a solvent.

| | |
|---|---|
| amount of ammonia: | based on 1 mole of compound [V], 1 mole to an excess amount |
| solvent: | 2-propanol, 2-methyl-2-propanol, or the like |
| temperature: | −10° C. to room temperature |
| time: | a moment (several seconds) to 48 hours |

After the completion of the reaction, the reaction mixture is poured into water and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be obtained.

6) Method to Produce Compound [VII] from Compound [V]

Compound [VII] may be produced by reacting compound [V] and aminoalcohol derivative [XII] given in Chemical Formula 6,

[Chemical Formula 6]

H$_2$N—G$^1$—OH

[Wherein, G$^1$ has the same definition as mentioned above] within a solvent or without solvent.

| | |
|---|---|
| amount of [XII]: | based on 1 mole of compound [V], 2 moles to an amount as solvent |
| solvent: | 2-propanol, 2-methyl-2-propanol, or the like |
| temperature: | −10° C. to temperature of reflux |
| time: | a moment (several seconds) to 72 hours |

After the completion of the reaction, the reaction mixture is poured into water and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

7) Method to Produce Compound [VIII] from Compound [VI]

Compound [III ] may be produced by reacting compound [VI] with compound [XIII], given in Chemical Formula 7,

[Chemical Formula 7]

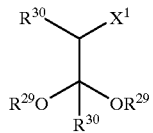

[XIII]

[Wherein, X$^1$ represents chlorine, bromine or iodine, R$^{29}$ represents C$_1$–C$_5$ alkyl, and R$^{30}$ has the same definition as mentioned above.]

in the presence of an acid, or with compound [XIV] given in Chemical Formula 8:

[Chemical Formula 8]

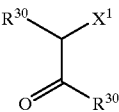

[XIV]

[Wherein, X$^1$ and R$^{30}$ have the same definition as mentioned above]

within a solvent or without solvent.

| | |
|---|---|
| amount of compound [XIII] or [XIV]: | based on 1 mole of compound [VI], 1 mole to an excess amount |
| solvent: | ethers such as dioxane, alcohols such as ethanol, organic acids such as acetic acid, water, or the like |
| temperature: | 0° C. to temperature of reflux |
| time: | a moment (several seconds) to 168 hours |
| sort of acid: | inorganic acids such as hydrochloric acid |
| amount of acid: | a catalytic amount to an excess amount |

After the completion of the reaction, the reaction mixture is poured into water if necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

8) Method to Produce Compound [IX] from Compound [VU]

Compound [IX] may be produced by reacting compound [VII] in the presence of an acid and usually without any solvent, but may be performed within a solvent if necessary.

| | |
|---|---|
| solvent: | ethers such as dioxane, alcohols such as ethanol, aromatic hydrocarbons such as benzene and toluene |
| temperature: | room temperature to reflux temperature |
| time: | a moment (several seconds) to 72 hours |
| sort of acid: | inorganic acids such as polyphosphoric acid and sulfuric acid |
| amount of acid: | a rate based on 1 mole of compound [VII], 1 mole to an excess amount |

After the completion of the reaction, the reaction mixture is neutralized with saturated sodium hydrogen carbonate solution after addition of water and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

Production Method 2

A production method that follows the scheme of Chemical Formula 9, given below may also be utilized to produce compounds of the invention.

[Chemical Formula 9]

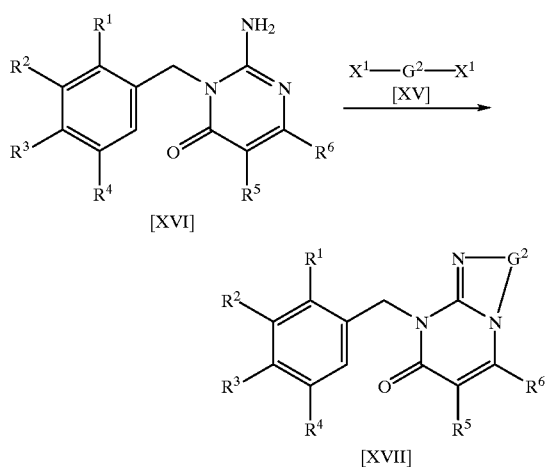

[Wherein, $R^1$, $R^2$, $R^3$, $R^4$, $R^5$, $R^6$ and $X^1$ have the same definition as mentioned above and, $G^2$ represents G-1 or G-2]

1.) Compound [XVII] May be Produced by Reacting Compound [XVI] and Compound [XV] Within a Solvent, and in the Presence of a Base.

| | |
|---|---|
| base: | alcoholates such as sodium ethoxide, organic bases such as triethylamine, or inorganic bases such as potassium carbonate |
| amount of base: | based on 1 mole of compound [XVI], 2 moles to an excess amount |

After the completion of the reaction, the reaction mixture (if necessary after addition of water) is neutralized with diluted hydrochloric acid and the precipitated crystals are collected by filtration, or the reaction mixture is subjected to ordinary post-treatment such as extraction with an organic solvent and concentration. If necessary, the purification procedure such as chromatography and recrystallization may be performed. Thus the objective material can be isolated.

Production Method 3

A production method by following the scheme of Chemical Formula 10, given below.

[Chemical Formula 10]

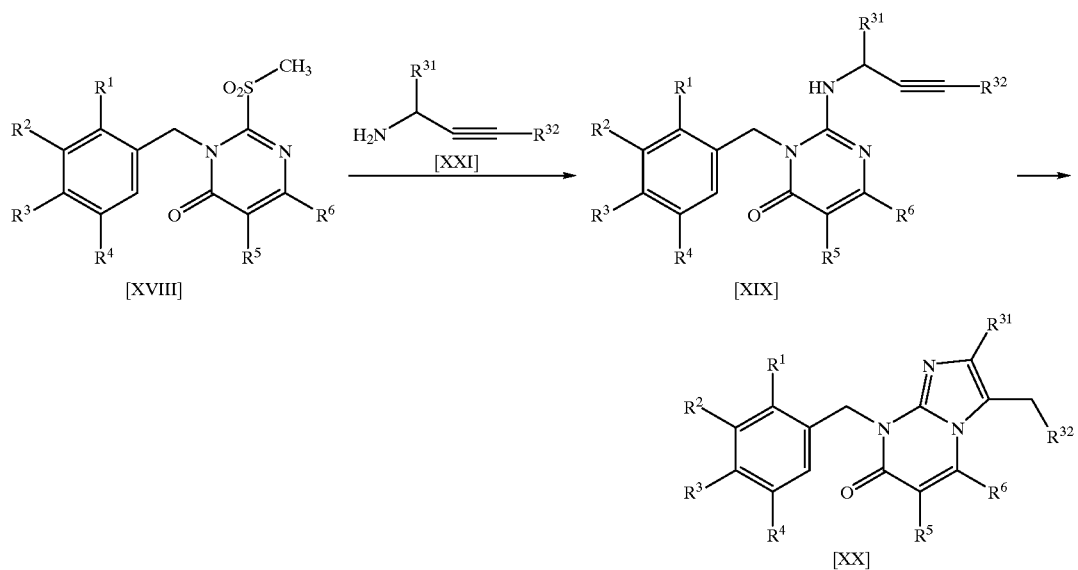

| | |
|---|---|
| Amount of compound [XV]: | based on 1 mole of compound [XVI], 1 mole to an excess amount |
| Solvent: | ethers such as dioxane, alcohols such as ethanol, water or the like |
| temperature: | 0° C. to reflux temperature |
| time: | a moment (several seconds) to 72 hours |

[Wherein, $R^1$, $R^2$, $R^3$, $R^4$, $R^5$, and $R^6$ have the same definition as mentioned above, $R^{31}$ represents hydrogen or $C_1$–$C_3$ alkyl, and $R^{32}$ represents hydrogen or $C_1$–$C_2$ alkyl.]

1) A Method to Produce Compound [XIX] from Compound [XVIII]

Compound [XIX] may be produced by reacting compound [XVIII] with compound [XXI] within or without a solvent.

| | |
|---|---|
| Amount of compound [XXI] | based on 1 mole of compound [XVIII], 1 mole to an amount as solvent |
| solvent: | 1,4-dioxane or N,N-dimethylformamide, or the like |
| temperature: | −20° C. to 100° C. |
| time: | a moment (several seconds) to 36 hours |

After the completion of the reaction, water is added to the reaction mixture if necessary, the precipitated crystals are collected by filtration, or the reaction mixture is subjected to ordinary post-treatment such as extraction with an organic solvent and concentration. If necessary, the purification procedure such as chromatography and recrystallization may be performed. Thus the objective material can be isolated.

2) A Method to Produce Compound [XX] from Compound [XIX]

Compound [XX] may be produced by reacting compound [XIX] in the presence of an acid.

| | |
|---|---|
| sort of acid: | sulfuric acid, or the like |
| temperature: | room temperature to 200° C. |
| time: | a moment (several seconds) to 24 hours |

After the completion of the reaction, water is added to the reaction mixture if necessary, and the precipitated crystals are collected by filtration, or the reaction mixture is subjected to ordinary post-treatment such as extraction with an organic solvent and concentration. If necessary, the purification procedure such as chromatography and recrystallization may be performed. Thus the objective material can be isolated.

Production Method 4

A production method that follows the scheme of Chemical Formula 11, given below.

[Chemical Formula 11]

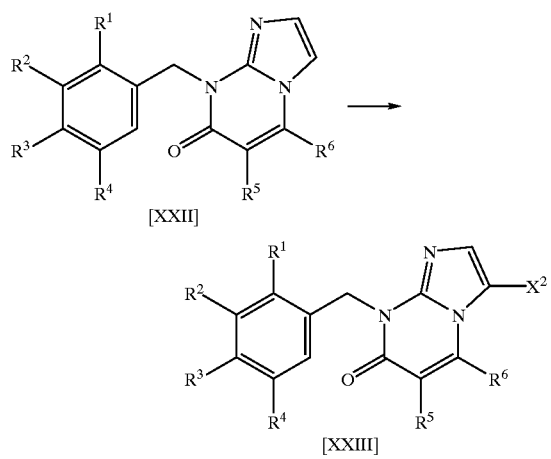

[XXII]

[XXIII]

[Wherein, $X^2$ represents chlorine, bromine or iodine, and $R^1$, $R^2$, $R^3$, $R^4$, $R^5$ and $R^6$ have the same definition as mentioned above.]

1) A Method to Produce Compound [XXIII] from Compound [XXII]

Compound [XXIII] may be produced by reacting compound [XXII] and a halogenating agent within a solvent.

| | |
|---|---|
| sort of solvent: | halogenated hydrocarbons such as chloroform or the like |
| sort of halogenating agent: | N-bromosuccinimide or N-chlorosuccinimide |
| amount of halogenating agent: | based on 1 mole of compound [XXII], 1 mole to an excess amount |
| temperature: | room temperature to temperature of reflux |
| time: | a moment (several seconds) to 24 hours |

After the completion of the reaction, the reaction mixture is subjected to ordinary post-treatment such as extraction with an organic solvent and concentration. If necessary, the purification procedure such as chromatography and recrystallization may be performed. Thus the objective material can be isolated.

Production Method 5

A production method that follows the scheme of Chemical Formula 12, given below.

[Chemical Formula 12]

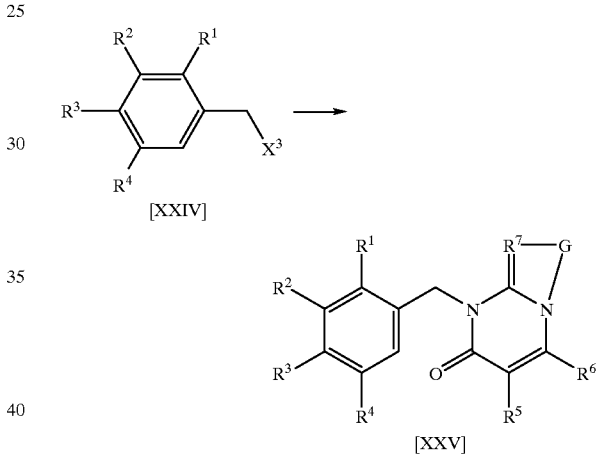

[XXIV]

[XXV]

[Wherein, $X^3$ represents chlorine or bromine, and $R^1$, $R^2$, $R^3$, $R^4$, $R^5$, $R^6$, $R^7$ and G have the same definition as mentioned above.]

1) A Method to Produce Compound [XXV] from Compound [XXIV]

Compound [XXV] may be produced by reacting compound [XXIV] and compound [XXVI], given in Chemical Formula 13:

[Chemical Formula 13]

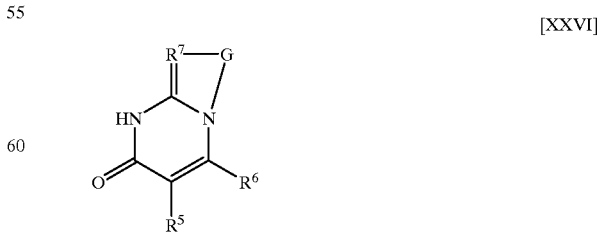

[XXVI]

[Wherein, $R^5$, $R^6$, $R^7$ and G have the same definition as mentioned above]

within a solvent and in the presence of a base.

| amount of compound [XXVI]: | based on 1 mole of compound [XXIV], 0.5 to 2 moles |
| --- | --- |
| sort of solvent: | dimethylformamide or tetrahydrofuran |
| sort of base: | inorganic bases such as sodium hydride |
| amount of base: | based on 1 mole of compound [XXIV], 1 mole to an excess amount |
| temperature: | −20° C. to temperature of reflux |
| time: | a moment (several seconds) to 24 hours |

After the completion of the reaction, water is poured into the reaction mixture and the precipitated crystals are collected by filtration, or the reaction mixture is subjected to ordinary post-treatment such as extraction with an organic solvent and concentration. If necessary, the purification procedure such as chromatography and recrystallization may be performed. Thus the objective material can be isolated.

Production Method 6

A production method that follows the scheme of Chemical Formula 14, given below.
[Chemical Formula 14]

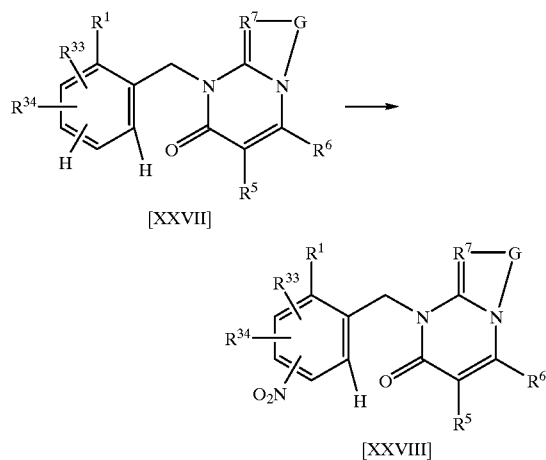

[Wherein, $R^{33}$ and $R^{34}$ are defined as 2 substituents from either $R^2$, $R^3$ and $R^4$ with the proviso that $NO_2$ is excluded; and $R^1$, $R^5$, $R^6$, $R^7$, and G have the same definition as mentioned above.]

1) Compound [XXVIII] May be Produced by Reacting Compound [XXVII] and Nitric Acid within a Solvent.

The limits for the reaction temperature of the said reaction is, usually from 0° C. to 100° C., and the limits for the reaction time is usually from a moment (several seconds) to 24 hours. For the amount of the agent used in the reaction, the theoretical amount is the rate of 1 mole of sulfuric acid per 1 mole of compound [XXVII], but may be optionally altered to correspond to the condition of the reaction. Solvent used include acidic solvents such as sulfuric acid.

After the completion of the reaction, the reaction mixture is added to water and the precipitated crystals are collected by filtration, or the reaction mixture added to water is extracted with an organic solvent and the organic layer is extracted and subjected to ordinary post-treatment such as concentration. If necessary, the purification procedure such as chromatography and recrystallization may be performed. Thus the objective material can be isolated.

Production Method 7

A production method that follows the scheme of Chemical Formula 15, given below.

[Chemical Formula 15]

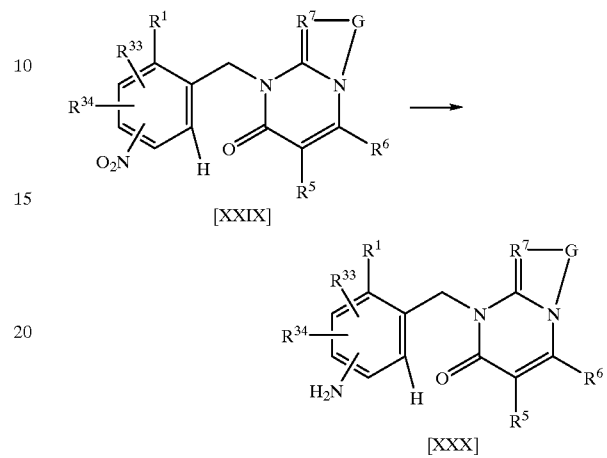

[Wherein, $R^1$, $R^5$, $R^6$, $R^7$, $R^{33}$, $R^{34}$ and G have the same definition as mentioned above.]

1) Compound [XXX] May be Produced by Reducing Compound [XXIX] within a Solvent. (cf. Organic Synthesis Collective Vol. 2, p.471 and vol. 5, p.829) The said reaction may be performed by incorporating compound [XXIX] or in a solution wherein compound [XXIX] is dissolved in a solvent such as ethyl acetate, to a mixture of, for example, acetic acid, iron powder and water. The limit of the reaction temperature is usually 0° C. to 100° C., and the limit of the reaction time is usually a moment (several seconds) to 24 hours.

After the completion of the reaction, the reaction mixture is filtered with sellaite, the filtrate is extracted with an organic solvent, the obtained organic layer is neutralized, and after that, the resultant is subjected to ordinary post-treatment such as concentration. If necessary, a purification procedure such as chromatography and recrystallization may be performed. Thus the objective material can be isolated.

Production Example 8

A production method that follows the scheme of Chemical Formula 16, given below.

[Chemical Formula 16]

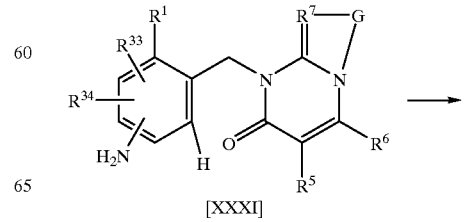

-continued

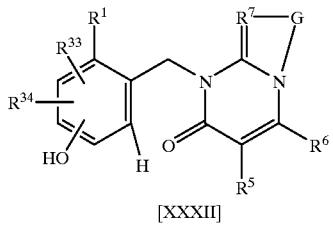

[XXXII]

[Wherein, $R^1$, $R^5$, $R^6$, $R^7$, $R^{33}$, $R^{34}$ and G have the same definition as mentioned above.]

1) Compound [XXXII] May be Produced by Previously Reacting Compound [XXXI] and Nitrite in a Solvent (reaction 1) and, thereafter, Heating in an Acidic Solvent (reaction 2).

| (reaction 1) | |
|---|---|
| nitrite: | sodium nitrite or potassium nitrite |
| amount of nitrite: | based on 1 mole of compound [XXXI], a rate of 1 to 2 moles |
| solvent: | aqueous hydrochloric acid or aqueous sulfuric acid |
| temperature | −10° C. to 10° C. |
| time: | a moment (several seconds) to 5 hours |
| (reaction 2) | |
| acidic solvent: | aqueous hydrochloric acid or aqueous sulfuric acid |
| temperature: | 70° C. to temperature reflux |
| time: | a moment (several seconds) to 24 hours |

After the completion of the reaction, water is added to the reaction mixture when necessary, and the precipitated crystals are collected by filtration, or the reaction mixture is subjected to ordinary post-treatment such as extraction with an organic solvent and concentration. If necessary, the purification procedure such as chromatography and recrystallization may be performed. Thus the objective material can be isolated.

Production Method 9

A production method that follows the scheme of Chemical Formula 17, given below.

[Chemical Formula 17]

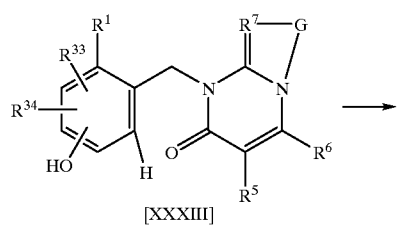

[XXXIII]

-continued

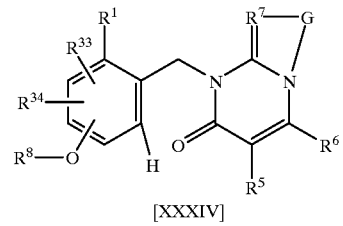

[XXXIV]

[Wherein, $R^1$, $R^5$, $R^6$, $R^7$, $R^8$, $R^{33}$, $R^{34}$ and G have the same definition as mentioned above.]

1) Compound [XXXIV] may be produced by reacting compound [XXXIII] and the compound having the formula $R^8$—D (wherein, D means chlorine, bromine, iodine, or a $CH_3SO_2O$ group) within a solvent and in the presence of a base. The reaction is usually performed in a solvent and, the limit of the reaction temperature is usually −20° to 150° C., preferably 0° C. to 100° C. The limit of the reaction time is usually a moment (several seconds) to 72 hours. For the amount of the agent used in the reaction, the theoretical amount is the rate of 1 mole each of the compound of formula $R^8$—D and the base 1 mole of compound [XXXIII], but may be optionally altered to correspond to the condition of the reaction.

As for the base that may be utilized in the reaction, organic and inorganic bases may both be utilized, and for example, potassium carbonate, sodium hydroxide and sodium hydride are set forth. As for the utilized solvent, aliphatic hydrocarbons such as hexane, heptane, ligroin, cyclohexane, petroleum ether; aromatic hydrocarbons such as benzene, toluene, xylene; halogenated hydrocarbons such as chloroform, carbon tetrachloride, dichloromethane, dichloroethane, chlorobenzene, dichlorobenzene; ethers such as diethyl ether, diisopropyl ether, dioxane, THF, ethylene glycol dimethyl ether; ketones such as acetone, methylethyl ketone, methylisobutyl ketone, isophorone, cyclohexanone; esters such as ethylformate, ethylacetate, butylacetate, diethylcarbonate; nitro compounds such as nitromethane, nitrobenzene; nitrites such as acetonitrile, isobutyronitrile; acid amides such as foramide, N,N-dimethylformamide (hereinafter, DMF), acetoamide; tertiary amines such as pyridine, triethylamine, diisopropylethylamine, N,N-dimethylaniline, N,N-diethylaniline, N-methylmorpholine; sulfur compounds such as dimethylsulfoxide, sulfonane and mixtures thereof are set forth.

After the completion of the reaction, water is added to the reaction mixture when necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

Production Method 10

A production method that follows the scheme of Chemical Formula 18, given below.

[Chemical Formula 18]

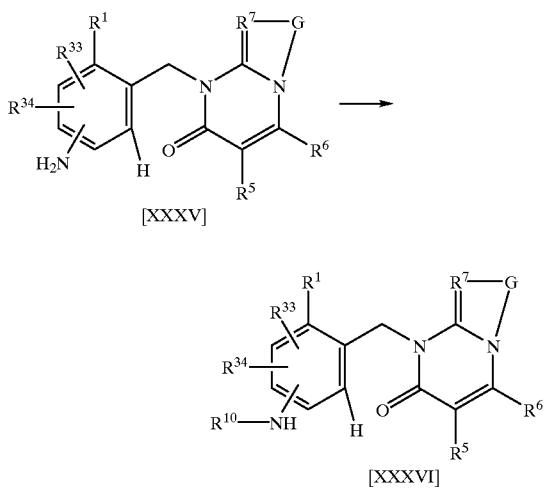

[Wherein, $R^1$, $R^5$, $R^7$, $R^{10}$, $R^{33}$, $R^1$, $R^{34}$ and G have the same definition as mentioned above.]

1) Compound [XXXVI] may be produced by reacting compound [XXXV] and a compound having the formula $R^{10}$—D (wherein, D has the same definition as mentioned above), within a solvent and in the presence of a base. The reaction is usually performed in a solvent and, the limit of the reaction temperature is usually from −20° to 150° C., preferably from 0° C. to 100° C. The limit to the reaction time is usually from a moment (several seconds) to 72 hours. For the amount of the agent used in the reaction, the theoretical amount is the rate of 1 mole each of the compound of the formula $R^{10}$—D and the base per 1 mole of compound [XXXV], but may be optionally altered to correspond to the condition of the reaction.

As for the base that may be utilized in the reaction, organic and inorganic bases may both be utilized, and for example, potassium carbonate, sodium hydroxide and sodium hydride etc. are set forth. As for the utilized solvent, aliphatic hydrocarbons such as hexane, heptane, ligroin, cyclohexane, petroleum ether; aromatic hydrocarbons such as benzene, toluene, xylene; halogenated hydrocarbons such as chloroform, carbon tetrachloride, dichloromethane, dichloroethane, chlorobenzene, dichlorobenzene; ethers such as diethyl ether, diisopropyl ether, dioxane, THF, ethylene glycol dimethyl ether; ketones such as acetone, methylethyl ketone, methylisobutyl ketone, isophorone, cyclohexanone; esters such as ethylformate, ethylacetate, butylacetate, diethylcarbonate; nitro compounds such as nitromethane, nitrobenzene; nitriles such as acetonitrile, isobutyronitrile, and so on; acid amides such as foramide, DME, acetoamide; tertiary amines such as pyridine, triethylamine, diisopropylethylamine, N,N-dimethylaniline, N,N-diethylaniline, N-methylmorpholine; sulfur compounds such as dimethylsulfoxide, sulforane; a mixture thereof; are set forth.

After the completion of the reaction, water is added to the reaction mixture when necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

Production Method 11

A production method that follows the scheme of Chemical Formula 19, given below is provided.

[Chemical Formula 19]

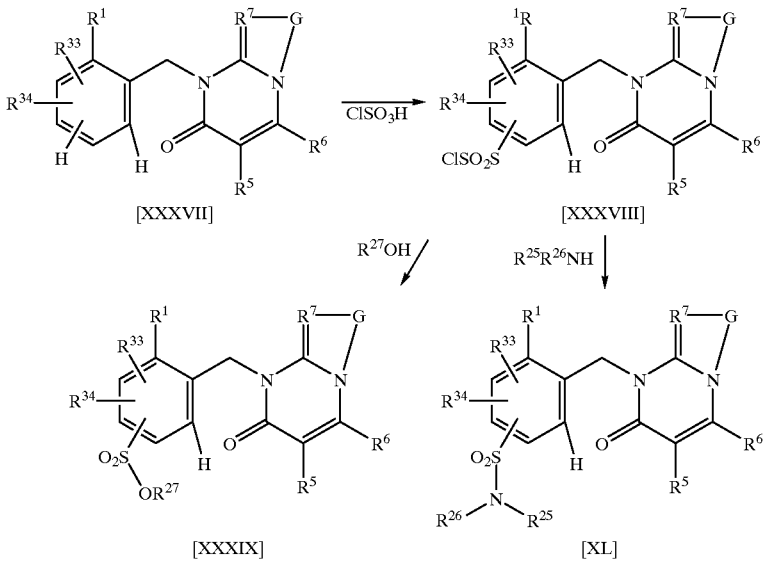

[Wherein, $R^1$, $R^5$, $R^6$, $R^7$, $R^{25}$, $R^{26}$, $R^{27}$, $R^{33}$, $R^{34}$ and G have the same definition as mentioned above.]

The reaction conditions, for example, of each step are given below.

1) A Method to Produce Compound [XXXVIII] from Compound [XXXVII]

Compound [XXXVIII] may be produced by reacting compound [XXXVII] and chlorosulfonic acid within or without a solvent.

| | |
|---|---|
| amount of chlorosulfonic acid: | based on 1 mole of compound [XXXVII], a rate of 1 mole to an excess amount |
| solvent: | sulfuric acid |
| temperature: | 0° C. to 70° C. |
| time: | a moment (several seconds) to 24 hours |

After the completion of the reaction, water is added to the reaction mixture when necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

(cf. Org. Syn. Coll. Vol.1,8 (1941))

2) A Method to Produce Compound [XXXIX] from Compound [XXXVIII]

Compound [XXXIX] may be produced by reacting compound [XXXVIII] and the compound given as $R^{27}$—OH (wherein, $R^{27}$ has the same definition as mentioned above) in the presence of a base and within or without a solvent.

| | |
|---|---|
| amount of $R^{27}$-OH: | based on 1 mole of compound [XXXVIII], a rate of 1 mole to an excess amount |
| base: | tertiary amines such as triethylamine or inorganic bases such as potassium carbonate |
| amount of base: | a rate of 1 to 2 moles |
| solvent: | DMF, 1,4-dioxane or the like |
| temperature: | 0° C. to 100° C. |
| time: | a moment to 24 hours |

After the completion of the reaction, water is added to the reaction mixture when necessary, and the precipitated crystals are collected by filtration, or the reaction mixture is subjected to ordinary post-treatment such as extraction with an organic solvent and concentration. If necessary, the purification procedure such as chromatography and recrystallization may be performed. Thus the objective material can be isolated.

3) A Method to Produce Compound [XL] from Compound [XXXVIII]

Compound [XL] may be produced by reacting compound [XXXVIII] and the compound having the formula $R^{25}R^{26}NH$ (wherein, $R^{25}$ and $R^{26}$ have the same definition as mentioned above) in the presence or absence of a base and within or without a solvent.

| | |
|---|---|
| amount of Compound $R^{25}R^{26}NH$: | based on 1 mole of compound [XXXVIII], a rate of 1 mole to an excess amount |
| base: | organic bases such as triethylamine or inorganic bases such as potassium carbonate |
| amount of base: | a rate of 1 to 2 moles |
| solvent: | DMF, 1,4-dioxane or the like |
| temperature: | 0° C. to 100° C. |
| time: | a moment (several seconds) to 24 hours |

After the completion of the reaction, water is added to the reaction mixture when necessary, and the precipitated crystals are collected by filtration, or the reaction mixture is subjected to ordinary post-treatment such as extraction with an organic solvent and concentration. If necessary, the purification procedure such as chromatography and recrystallization may be performed. Thus the objective material can be isolated.

Production Method 12

A production method that follows the scheme of Chemical Formula 20, given below.

[Chemical Formula 20]

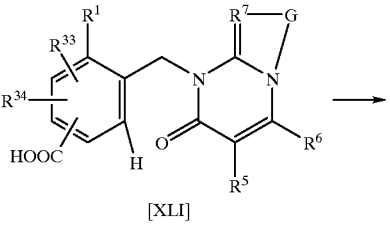

[XLI]

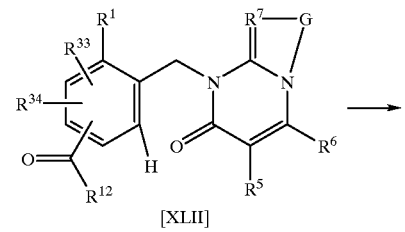

[XLII]

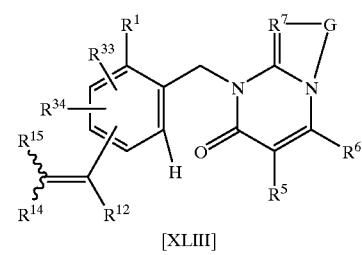

[XLIII]

[Wherein, $R^1$, $R^5$, $R^6$, $R^7$, $R^{12}$, $R^{14}$, $R^{15}$, $R^{33}$, $R^{34}$ and G have the same definition as mentioned above. However, the situation when $R^{12}$ is hydrogen or halogen is excluded]

1) A Method to Produce Compound [XLII] from Compound [XLI]

Compound [XLII] may be produced from compound [XLI] by following the method reported in Japanese patent publication (laid-open) hei-5-294920.

2) A Method to Produce Compound [XIII] from [XLII]

Compound [XLII] may be produced by reacting compound [XLII] and either compound having the formula $(C_6H_5)_3P=CR^{14}R^{15}$ or $(C_2H_5O)_2P(O)CHR^{14}R^{15}$ (wherein, $R^{14}$ and $R^{15}$ have the same definition as mentioned above) within a solvent and, in the absence of a base when utilizing the compound of the formula $(C_6H_5)_3P=CR^{14}R^{15}$, and in the presence of a base when utilizing the compound of the formula $(C_2H_5O)_2P(O)CHR^{14}R^{15}$

| | |
|---|---|
| amount of the compound of the formula $(C_6H_5)_3P=CR^{14}R^{15}$ or the compound of the formula $(C_2H_5O)_2P(O)CHR^{14}R^{15}$: | based on 1 mole of compound [XLII], a rate of 1 to 2 moles |
| solvent: | THF, toluene or the like |
| base: | sodium hydride or the like |
| amount of base: | based on 1 mole of compound [XLII], a rate of 1 to 2 moles |
| temperature: | 0° C. to 50° C. |
| time: | a moment to 24 hours |

After the completion of the reaction, water is added to the reaction mixture when necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

Production Method 13

A production method that follows the scheme of Chemical Formula 21, given below.

[Chemical Formula 21]

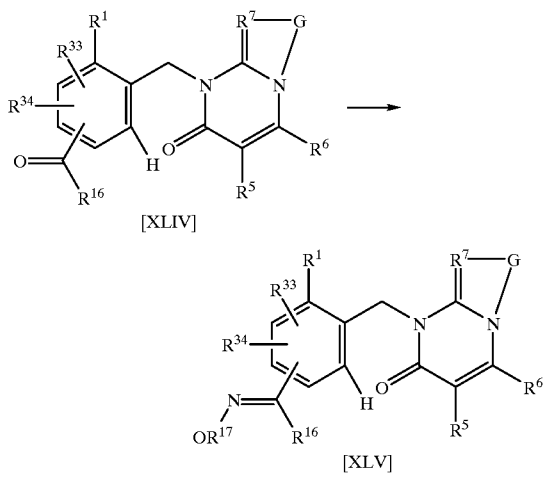

[Wherein, $R^1$, $R^5$, $R^6$, $R^7$, $R^{16}$, $R^{17}$, $R^{33}$ $R^{34}$ and G have the same definition as mentioned above.]

1) Compound [XLV] may be produced by reacting the compound [XLIV] and a compound of the formula $H_2N$—O—$R^{17}$ (wherein, $R^{17}$ has the same definition as mentioned above).

The reaction is performed within either a lower alcohol such as methanol, ethanol and isopropanol, or a mixture of a lower alcohol and water. The limit to the reaction temperature is 0° C. to 80° C., and the limit of the reaction time is a moment (several seconds) to 72 hours.

For the amount of the compound having the formula $H_2N$—O—$R^{17}$ used in the reaction, the theoretical amount is the rate of 1 mole per 1 mole of compound [XLIV], but may be optionally altered to correspond to the conditions of the reaction.

The compound having the formula $H_2N$—O—$R^{17}$ may be utilized in the form of a salt of an acid additive such as hydrochloride and sulfate.

The present reaction may also be performed by adding organic bases such as pyridine; alkali metal carbonates such as sodium carbonate, potassium carbonate; alkali metal hydrogencarbonate such as sodium hydrogencarbonate; alkali earth metal carbonates such as calcium carbonate; and so on.

After the completion of the reaction, water is added to the reaction mixture when necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

Production Method 14

A production method that follows the scheme of Chemical Formula 22, given below.

[Chemical Formula 22]

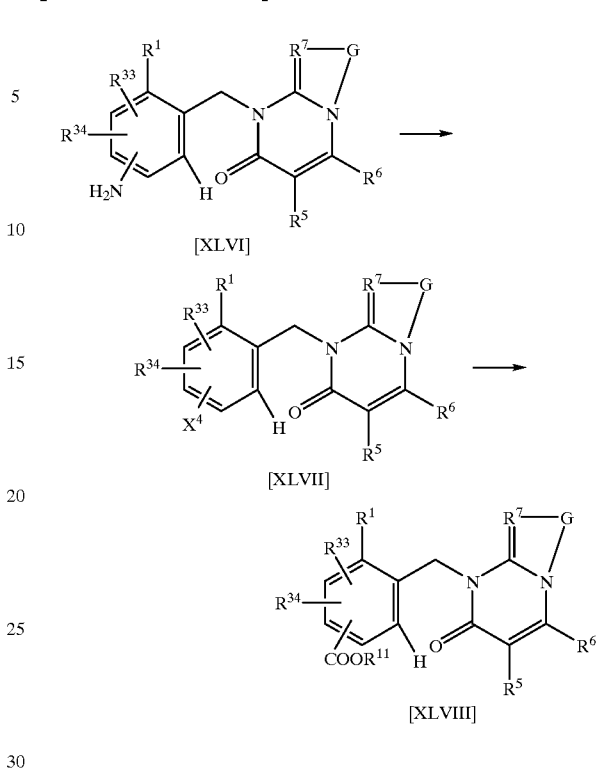

[Wherein, $R^1$, $R^5$, $R^6$, $R^7$, $R^{11}$, $R^{33,}$ $R^{34}$ and G have the same definition as mentioned above, and $X^4$ represents bromine or iodine.]

The reaction conditions, for example, of each step are given below.

1) A Method to Produce Compound [XLVII] from Compound [XLVI]

Compound [XLVII] may be produced by previously diazotizing compound [XLVI] within a solvent (reaction 1), and thereafter, reacting with potassium iodide or copper(I) bromide within a solvent (reaction 2).

| (reaction 1) | |
|---|---|
| diazotization agent: | sodium nitrite or potassium nitrite |
| amount of diazotization agent: | based on 1 mole of compound [XLVI], a rate of 1 to 2 moles |
| sort of solvent: | aqueous hydrogen bromide, aqueous sulfuric acid or the like |
| temperature: | −10° C. to 10° C. |
| time: | a moment (several seconds) to 5 hours |
| (reaction 2) | |
| amount of potassium iodide or copper (I) bromide: | based on 1 mole of compound [XLVI], 1 mole to an excess amount |
| solvent: | aqueous hydrogen bromide or aqueous sulfuric acid |
| temperature: | 0° C. to 80° C. |
| time: | a moment (several seconds) to 24 hours |

After the completion of the reaction, water is added to the reaction mixture when necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

(cf. Org. Syn. Coll. Vol. 2, 604 (1943), Vol. 1, 136 (1932))

2) A Method to Produce Compound [XLVIII] from Compound [XLVII]

Compound [XLVIII] may be produced by reacting compound [XLVII], carbon monoxide, and a compound having the formula $R^{11}$—OH (wherein, $R^{11}$ has the same definition as mentioned above) within a solvent, and in the presence of a transition metal catalyst and base.

| | |
|---|---|
| catalyst: | $PdCl_2$ $(PPh_3)_2$ (wherein, Ph represents phenyl), or the like |
| amount of catalyst: | based on 1 mole of compound [XLVII], a rate of catalytic amount to 0.5 moles |
| amount of $R^{11}$-OH: | based on 1 mole of compound [XLVII], a rate of 1 mole to an excess amount |
| base: | organic bases such as diethylamine |
| amount of base: | based on 1 mole compound [XLVII], a rate of 1 to 2 moles |
| solvent: | DMF |
| atmospheric pressure of carbon monoxide: | 1 to 150 atmospheres |
| temperature: | 0° C. to 100° C. |
| time: | instantaneous to 72 hours |

After the completion of the reaction, water is added to the reaction mixture when necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

(cf. Bull. Chem. Soc. Jpn. 48 (7), 2075 (1975))

Production Method 15

A production method that follows the scheme of Chemical Formula 23, given below.
[Chemical Formula 23]

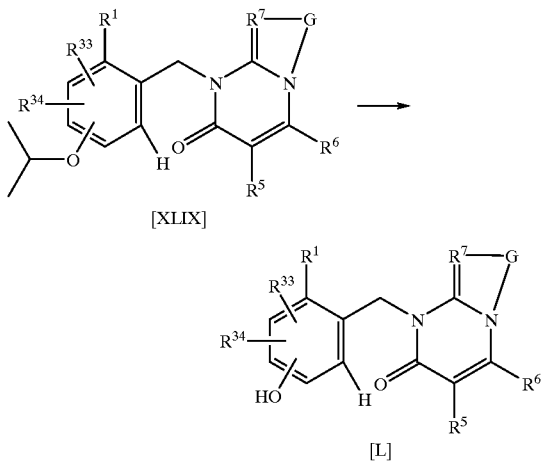

[Wherein, $R^1$, $R^5$, $R^6$, $R^7$, $R^{33}$, $R^{34}$ and G have the same definition as mentioned above.]

1) Compound [L] may be produced by hydrolyzing compound [XLIX] either in the presence of an acid such as sulfuric acid, or treating it with an acid such as boron tribromide within a solvent such as methylene chloride, and then with water.

The limit to the reaction temperature is usually from −20° C. to 150° C., preferably from 0° C. to 100° C., and the limit to the reaction time is usually from a moment (several seconds) to 72 hours. The amount of the acid used in the reaction theoretically follows the rate of 1 mole per 1 mole of compound [XLIX], but may optionally be altered to correspond to the conditions of the reaction.

After the completion of the reaction, water is added to the reaction mixture when necessary, and the precipitated crystals are collected by filtration, or the reaction mixture is subjected to ordinary post-treatment such as extraction with an organic solvent and concentration. If necessary, a purification procedure such as chromatography and recrystallization may be performed. Thus the objective material can be isolated.

Production Method 16

A production method that follows the scheme of Chemical Formula 24, given below.
[Chemical Formula 24]

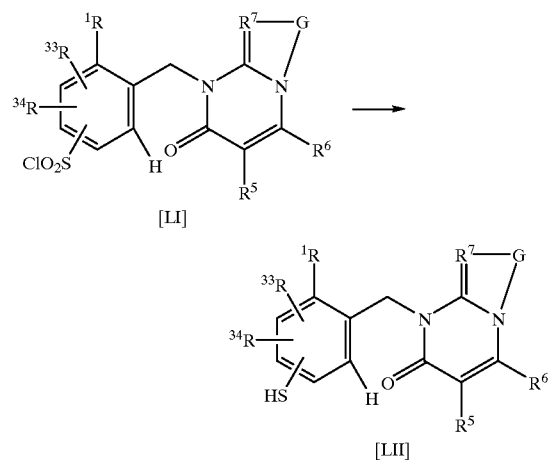

[Wherein, $R^1$, $R^5$, $R^6$, $R^7$, $R^{33}$, $R^{34}$ and G have the same definition as mentioned above.]

1) Compound [LII] may be produced from compound [LII] by following the method reported in Japanese patent publication (laid-open) sho 60-248657.

Hereinafter, the intermediates or raw materials utilized when producing the present invention compound are discussed.

The raw material used when producing the present invention compound by means of Production Method 5 is the pyrimidine derivative given in Chemical Formula 25 and may be produced, for example, by following Production Method 17, given below.
[Chemical Formula 25]

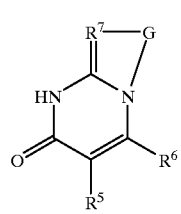

[XXVI]

[Wherein, $R^5$, $R^6$, $R^7$ and G have the same definition as mentioned above.]

Production Method 17

A method wherein the compound [LIII] given in Chemical Formula 26:

[Chemical Formula 26]

[LIII]

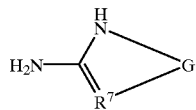

[Wherein, G and $R^7$ have the same definition as mentioned above.]

is reacted with one of either the ester derivative given in Chemical Formula 27:

[Chemical Formula 27]

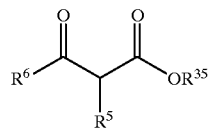

[Wherein, $R^5$ and $R^6$ have the same definition as mentioned above, and $R^{35}$ represents $C_1$–$C_6$ alkyl.]

or the enolether derivative given in Chemical Formula 28:

[Chemical Formula 28]

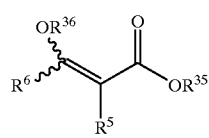

[Wherein, $R^5$, $R^6$ and $R^7$ have the same definition as mentioned above, and $R^{36}$ represents $C_1$–$C_3$ alkyl.].

The reaction is usually performed within or without a solvent, and the limit of the reaction temperature is usually 50° C. to 200° C., and the limit of the reaction time is usually 1 to 100 hours. For the amount of the agent used in the reaction, based on 1 mole of compound [LIII] given in Chemical Formula 26, the amount of the ester derivative given in Chemical Formula 27 or the enolether derivative given in Chemical Formula 28 is theoretically the rate of 1 mole, but may be optionally altered to correspond to the conditions of the reaction. As for the utilized solvent, aliphatic hydrocarbons such as hexane, heptane, octane, ligroin; aromatic hydrocarbons such as benzene, toluene, ethylbenzene, xylene, mesitylene; halogenated hydrocarbons such as chlorobenzene, dichlorobenzene, trichlorobenzene; ethers such as 1,4-dioxane, tetrahydrofuran, ethylene glycol dimethyl ether, methyl-t-butyl ether; nitro compounds such as nitromethane, nitrobenzene; acid amides such as N,N-dimethylformamide; sulfur compounds such as dimethylsulfoxide, sulforane; a mixture thereof; and so on are set forth. In addition, an acid such as para-toluenesulfonic acid may be utilized in the reaction as a catalyst.

After the completion of the reaction, the reaction mixture is subjected to a concentration procedure or the reaction mixture is subjected to ordinary post-treatment such as addition into water, extraction with an organic solvent and drying or concentrating the organic layer. If necessary, the purification procedure such as column chromatography and recrystallization may be performed. Thus the objective compound [XXVI] can be obtained.

The raw material used when producing the present invention compound by means of Production Method 5 is the benzylhalide derivative given in Chemical Formula 29:

[Chemical Formula 29]

[XXIV]

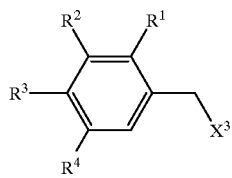

[Wherein, $X^3$ represents chlorine or bromine, and $R^1$, $R^2$, $R^3$, and $R^1$ have the same definition as mentioned above]

and may be produced, for example, by following the method disclosed in *Jikken Kaeaku Kouza* 19 (4$^{th}$ edition, Japan Chemical Society version, Maruzen Company Ltd. Pg 428–429).

Poduction Method 19

The raw material used when producing the present invention compound by means of Production Method 1 is the benzyl amine derivative given in Chemical Formula 30:

[Chemical Formula 30]

[I]

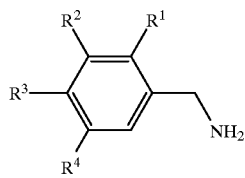

[Wherein, $R^1$, $R^2$, $R^3$ and $R^4$ have the same definition as mentioned above]

and may be produced, for example, by the scheme in Chemical Formula 31, given below.

[Chemical Formula 31]

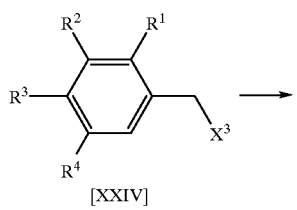

[XXIV]

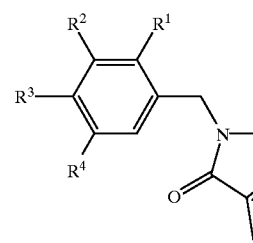

[LVI]

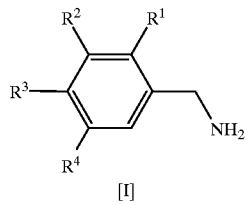

[Wherein, $R^1$, $R^2$, $R^3$ and $R^4$ and $X^3$ have the same definition as mentioned above]

1) Compound [LVI] may be obtained by reacting the benzylhalide derivative given as compound [XXIV] and a phthalimide in the presence of a base, usually within a solvent. The limits to the reaction temperature are usually from 0 to 200° C. and the limits to the reaction time are usually from 1 to 100 hours in the said reaction. As for the base that may be utilized in the reaction, inorganic bases such as sodium hydride, potassium carbonate, are set forth. The amount of base is theoretically the rate of 1 mole per 1 mole of compound [XXIV], but may be optionally altered to correspond to the condition of the reaction; and the amount of the phthalimide used in the reaction is theoretically the rate of 1 mole per 1 mole of compound [XXIV], but may also be optionally altered to correspond to the condition of the reaction.

As for the solvent, dimethylformamide, DME and the like are set forth.

After the completion of the reaction, the reaction mixture is subjected to a concentration procedure or the reaction mixture is subjected to ordinary post-treatment such as addition into water, extraction with an organic solvent and drying or concentrating the organic layer. If necessary, a purification procedure such as column chromatography and recrystallization may be performed. Thus the objective compound [LVI] can be obtained.

2) Compound [I] may be obtained by reacting compound [LVI] and hydrazine hydrate usually within a solvent. The limits to the reaction temperature are usually from −10° C. to 100° C. and the limits to the reaction time are usually from 1 to 100 hours for the reaction. The amount of hydrazine hydrate used in the reaction is theoretically the rate of 1 mole per 1 mole of compound [LVI], but may be optionally altered to correspond to the condition of the reaction.

As for the solvent, methanol, ethanol, isopropanol, and so on are set forth.

After the completion of the reaction, the reaction mixture is subjected to a concentration procedure or the reaction mixture is subjected to ordinary post-treatment such as addition into water, extraction with an organic solvent and drying or concentrating the organic layer. If necessary, a purification procedure such as column chromatography, recrystallization and distillation may be performed. Thus the objective compound [I] can be obtained.

In addition, the benzylhalide derivative given as compound [XXIV] and the benzylamine derivative given as compound [I] are in the public knowledge from, for example, USP5683966, WO9504461, WO 9735845 or WO9747607, or may be produced by following the methods reported therein.

The present inventive compounds possess an excellent herbicidal effectiveness, and hence some of them show excellent selectivity between crops and weeds. More particularly, the present inventive compounds, on foliar treatment or soil treatment, possess excellent herbicidal activity against the following variety of weeds which cause troublesome.

Polygonaceous Weeds:
  wild buckwheat (*Polygonum convolvulus*), pale smartweed (*Polygonum lapathifolium*), pennsylvania smartweed (*Polygonum pensylvanicum*), ladysthumb (*Polygonumpersicaria*), curly dock (*Rumex crispus*), broadleaf dock (*Rumex obtusifolius*), Japanese knotweed (*Polygonum cuspidatum*)
Portulacaceous Weeds:
  common purslane (*Portulaca oleracea*)
Caryophyllaceous Weeds:
  common chickweed (*Stellaria media*)
Chenopodiaceous Weeds:
  common lambsquarters (*Chenopodium album*), kochia (*Kochia scoparia*)
Amaranthaceous Weeds:
  redroot pigweed (*Amaranthus retroflexus*), smooth pigweed (*Amaranthus hybridus*)
Cruciferous (brassicaceous) Weeds:
  wild radish (*Raphanus raphanistrum*), wild mustard (*Sinapis arvensis*), shepherdpurse (*Capsella bursa-pastoris*)
Leguminous (fabaceous) Weeds:
  hemp sesbania (*Sesbania exaltata*), sicklepod (*Cassia obtusifolia*), Florida beggarweed (*Desmodium tortuosum*), white clover (*Trifolium repens*)
Malvaceous Weeds:
  velvetleaf (*Abutilon theophrasti*), prickly sida (*Sida spinosa*)
Violaceous Weeds:
  field pansy (*Viola arvensis*), wild pansy (*Viola tricolor*)
Rubiaceous Weeds:
  catchweed bedstraw (cleavers) (*Galium aparine*)
Convolvulaceous Weeds:
  ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)
Labiate Weeds:
  red deadnettle (*Lamium purpureum*), henbit (*Lamium amplexicaule*)
Solanaceous Weeds:
  jimsonweed (*Datura stramonium*), black nightshade (*Solanum nigrum*)
Scrophulariaceous Weeds:
  birdseye speedwell (*Veronica persica*), ivyleaf speedwell (*Veronica hederaefolia*)
Composite Weeds:
  common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)
Boraginaceous Weeds:
  forget-me-not (*Myosotis arvensis*)
Asclepiadaceous Weeds:
  common milkweed (*Asclepias syriaca*)
Euphorbiaceous Weeds:
  sun spurge (*Euphorbia helioscopia*), spotted spurge (*Euphorbia maculata*)

Graminaceous Weeds:

barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)

Commelinaceous Weeds:

common dayflower (*Commelina communis*)

Equisetaceous Weeds:

field horsetail (*Equisetum arvense*)

Cyperaceous Weeds:

rice flatsedge (*Cyperus iria*), purple nutsedge (*Cyperus rotundus*), yellow nutsedge (*Cyperus esculentus*)

Furthermore, some of the present invention compounds exhibit no significant phytotoxicity on the main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*), and canola (*Brassica napus*); horticultural crops such as flowers and ornamental plants; and vegetables.

Various weeds that may cause some trouble in the no-tillage cultivation of soybean (*Glycine max*), corn (*Zea mays*), wheat (*Triticum aestivum*), or the like, andmay be efficaciously controlled by the present inventive compounds. Furthermore, some of the present inventive compounds exhibit no significant phytotoxicity on the crops.

The present invention compounds also have herbicidal activity against various weeds which may cause some trouble in the flooding treatment on paddy fields, such as the listed below.

Graminaceous Weeds:

barnyardgrass (*Echinochloa oryzicola*)

Scrophulariaceous Weeds:

common falsepimpernel (*Lindernia procumbens*)

Lythraceous Weeds:

Indian toothcup (*Rotala indica*), red stem (*Ammannia multiflora*)

Elatinaceous Weeds:

waterwort (*Elatine triandra*)

Cyperaceous Weeds:

smallflower umbrella sedge (*Cyperus difformis*), hardstem bulrush (*Scirpus juncoides*), needle spikerush (*Eleocharis acicularis*), water nutgrass (*Cyperus serotinus*), water chestnut (*Eleocharis kuroguwai*)

Pontederiaceous Weeds:

monochoria (*Monochoria vaginalis*)

Alismataceous Weeds:

arrowhead (*Sagittaria pygmaea*), arrowhead (*Sagittaria trifolia*), waterplantain (*Alisma canaliculatum*)

Potamogetonaceous Weeds:

roundleaf pondweed (*Potamogeton distinctus*)

Umbelliferous Weeds:

watercelery sp. (*Oenanthe javanica*)

Furthermore, some of the present invention compounds exhibit no significant phytotoxicity on transplanted paddy rice.

The present inventive compounds can also control a wide variety of weeds which grow or will grow in the orchards, grasslands, lawns, forests, waterways, canals, or other uncultivated lands. In addition, the present inventive compounds also possess herbicidal activity against aquatic weeds, such as water hyacinth (*Eichhornia crassipes*), which grow or will grow in waterways or canals.

The present compounds of the invention have substantially the same characteristics as those of the herbicidal compounds disclosed in the published specification of International Patent publication WO95/34659. In the case of cultivating crops wherein tolerance is bestowed to the said crops by introducing a herbicide tolerance gene described in the said specification, the present inventive compound can be used at larger amount than those used when ordinary crops without tolerance are cultivated, thus making it possible to control other unfavorable weeds more effectively.

When one of the present inventive compounds is used as the active ingredient of a herbicide, the inventive compound is usually mixed with solid or liquid carriers, surfactants, and other auxiliary agents to give emulsifiable concentrates, wettable powders, flowables, granules, concentrated emulsions, water-dispersible granules, or other formulations.

These formulations may comprise a compound of present invention as an active ingredient at an amount from 0.001% to 80% by weight, preferably from 0.005% to 70% by weight.

The solid carrier may include, for example, fine powders or granules of the following materials: mineral fine powders such as kaolin clay, attapulgite clay, bentonite, acid clay, pyrophyllite, talc, diatomaceous earth, and calcite; organic fine powders such as walnut shell powder; water-soluble organic fine powders such as urea; fine powders of inorganic salts such as ammonium sulfate; and fine powders of synthetic hydrated silicon oxide.

The liquid carrier may include, for example, aromatic hydrocarbons such as methylnaphthalene, phenylxylylethane, and alkylbenzene (e.g., xylene); alcohols such as isopropanol, ethylene glycol and 2-ethoxyethanol; esters such as dialkyl ester phthalate; ketones such as acetone, cyclohexanone, and isophorone; mineral oils such as machine oil; vegetable oils such as soybean oil and cottonseed oil; dimethylsulfoxide, N,N-dimethylformamide, acetonitrile, N-methylpyrrolidone, and water.

As the surfactant used for emulsion, dispersing or spreading; anionic surfactants such as alkylsulfate salts, alkylsulfonate salts, alkylarylsulfonate salts, dialkylsulfosuccinate salts and polyoxyethylene alkylarylether phosphate salts and nonionic surfactants such as polyoxyethylene alkylether, polyoxyethylene alkylarylether, polyoxyethylene polyoxypropylene block copolymers, sorbitan fatty acid esters and polyoxyethylene sorbitan fatty acid ester are set forth.

Lignin sulfonates, alginates, polyvinyl alcohol, gum arabic, CMC (carboxymethylcellulose), and PAP (isopropyl acid phosphate) and the like are set forth as the possible auxiliary agents, for example.

The present inventive compounds are usually formulated and then used for soil treatment before or after the emergence of weeds. The soil treatment may include a soil surface treatment and a soil incorporation treatment. The foliar treatment may include application over the plants and directed application in which it is applied only to weeds, so as to keep the same off the crop plants.

Furthermore, by intermixing with other herbicides, there are situations wherein an enhanced herbicidal efficacy is confirmed. Furthermore, the present inventive compounds may be used in a admixture with insecticides, acaricides, nematocides, fungicides, bactericides, plant growth regulators, fertilizers, and soil improvements.

Examples of the herbicides are atrazine, cyanazine, dimethametryn, metribuzin, prometryn, simazine, simetryn, chlorotoluron, diuron, dymron, fluometuron, isoproturon, linuron, methabenzthiazuron, bromoxynil, ioxynil, ethalfluralin, pendimethalin, trifluralin, acifluorfen, acifluorfen-sodium, bifenox, chlomethoxynil, fomesafen, lactofen, oxadiazon, oxadiargyl, oxyfluorfen, carfentrazone-ethyl, flumiclorac-pentyl, flumioxazine, fluthiacet-methyl, sulfentrazone, thidiazimin, azafenidin, pyraflufen-ethyl, cinidon-ethyl, difenzoquat, diquat, paraquat, 2,4-D, 2,4-DB, DCPA, MCPA, MCPB, clomeprop, clopyralid, dicamba, dithiopyr, fluroxypyr, mecoprop, naploanilide, phenothiol, quinclorac, triclopyr, thiazopyr, acetochlor, alachlor, butachlor, diethatyl-ethyl, metolachlor, pretilachlor, propachlor, bensulfuron-methyl, chlorsulfuron, chlorimuron-ethyl, halosulfuron-methyl, metsulfuron-methyl, nicosulfuron, primisulfuron-methyl, pyrazosulfuron-ethyl, sulfometuron-ethyl, thifensulfuron-methyl, triasulfuron, tribenuron-methyl, oxasulfuron, iodosulfuron, azimsulfuron, cloransulam-methyl, cyclosulfamuron, flumetsulam, flupyrsulfuron, flazasulfuron, imazosulfuron, metosulam, diclosulam, prosulfuron, rimsulfuron, triflusulfuron-methyl, ethoxysulfuron, sulfosulfuron, imazamethabenz-methyl, imazapyr, imazaquin, imazethapyr, imazameth, imazamox, flucarbazone, pyribenzoxim, bispyribac-sodium, pyriminobac-methyl, pyrithiobac-sodium, alloxydim-sodium, clethodim, sethoxydim, tralkoxydim, tepraloxydim, dichlofop-methyl, fenoxaprop-ethyl, fenoxaprop-p-ethyl, fluazifop-butyl, fluazifop-p-butyl, haloxyfop-methyl, quizalofop-p-ethyl, cyhalofop-butyl, clodinafop-propargyl, benzofenap, clomazone, diflufenican, norflurazon, pyrazolate, pyrazoxyfen, flurtamone, isoxaflutole, sulcotrione, mesotrione, isoxachlortole, glufosinate-ammonium, glyphosate, bentazone, benthiocarb, bromobutide, butamifos, butylate, dimepiperate, dimethenamid, fentrazamide, DSMA, EPTC, esprocarb, isoxaben, mefenacet, molinate, MSMA, piperophos, pyributicarb, propanil, pyridate, triallate, cafenstrol, flupoxam, fluthiamide, diflufenzopyr, triaziflam, pentoxazone, epoprodan, metobenzuron, and oxaziclomefone, isopropazole, indanofen.

The above compounds are disclosed in the catalog of Farm Chemicals Handbook, 1995 (published by Meister Publishing Company); AG CHEM NEW COMPOUND REVIEW, VOL. 13, 1995, VOL. 15, 1997 and VOL. 16, 1998 (published by AG CHEM INFORMATION SERVICES); and "Josouzai Kenkyu Souran" (published by Hakuyu-sha).

In the case when the present invention compound is utilized as an active ingredient of an herbicide, the application amount may vary with the weather conditions, formulation types, application timing, application method, soil conditions, objective crop or crops, objective weed or weeds, and so on, but is usually applied at 0.01 g to 20,000 g per hectare, preferably 1 g to 2,000 g per hectare. When the present invention compound is formulated into emulsifiable concentrates, wettable powders, flowables, concentrated emulsions, water-dispersible granules, or the like, the said formulations are applied by diluting the present compound invention usually in 10L to 1000L of water (if necessary, the water may include an adjuvant such as a spreading agent) so the prescribed amount of the active ingredient can be applied to each hectare. Granule formulations and some types of flowables are usually applied without diluting.

The adjuvant which can be used herein, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed oil, and sunflower oil. The present invention compounds can also be used as the active ingredients of harvesting aids such as defoliants and desiccants for cotton (Gossipyum spp.), and desiccants for potato (Solanum tuberosum). In these cases, the present invention compounds are usually formulated in the same manner as the case where they are used as the active ingredients of herbicides, and may be used alone or in admixture with other harvesting aids for foliar treatment before harvesting the crops.

Hereinafter, the present invention is explained more specifically by means of the production examples, formulation examples and test examples, but the said examples do not limit the present invention in any way. Based on each example, the present invention compound is represented in the following Tables 1 through 4 as compound numbers.

PRODUCTION EXAMPLE 1 (the production of the present invention compound 2-1)

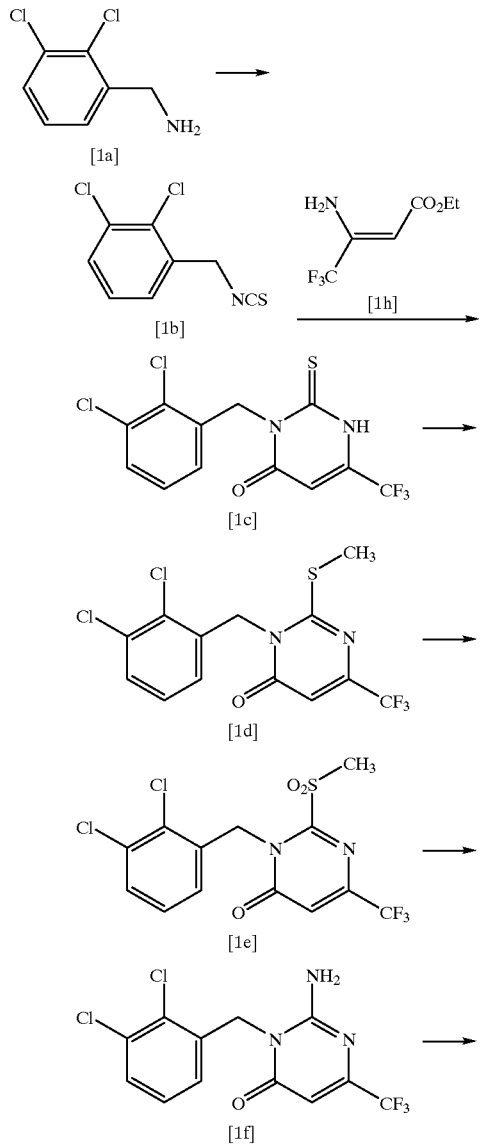

-continued

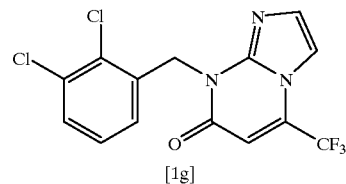
[1g]

1) Ten grams (10 g) of compound [1a] was dissolved in 100 mL of toluene. After adding 7.2 g of thiophosgene and heating under reflux for 3 hours, the reaction mixture was concentrated to obtain 12.2 g of compound [1b].

2) To a solution wherein 3.4 g of sodium hydride is suspended in 10 mL of dimethylformamide, 12.5 g of compound [1 h] was added dropwise at 5° C. or less and, was then stirred at room temperature for 30 min. Subsequently, 12.2 g of compound [1b] was added dropwise. After the completion of the addition, the reaction mixture was left or 2 days and then, it was incorporated into water and extracted with diethylether. The aqueous layer was then neutralized with diluted hydrochloric acid and extracted by utilizing diethylether. The obtained organic layer was washed by employing a saturated aqueous solution of sodium chloride, thereupon dried and concentrated to obtain crystals that was later washed with a mixed solvent comprising hexane and diethylether at the ratio of 4:1, to give 14.3 g of compound [1c].

[$^1$H-NMR(250 MHz, CDCl$_3$, TMS δ (ppm)) 5.68(2H, s), 6.36(1H, s), 6.78 to 6.82 (1H, m), 7.13 (1H, dd, J=7.96 Hz), 7.37 to 7.41 (1H, m), 8.06 (1H, S)]

3) After 13.3 g of compound [1c] was dissolved in 50 mL of dimethylformamide, 5.7 g of triethylamine was incorporated and cooled to 10° C. Eight grams (8.0 g) of iodomethane was then incorporated and stirred for 1 hour. Subsequently, the reaction mixture was poured into water, extracted with diethylether, washed by employing diluted hydrochloric acid, and thereupon dried and concentrated to obtain a residue that was later subjected to silica gel chromatography (eluent; hexane: ethyl acetate=7:1) to obtain 9.14 g of compound [1d].

[$^1$H-NMR(250 MHz, CDCl$_3$, TMS δ (ppm)) 2.57(3H, s), 5.42(2H, s), 6.65(1H, s), 6.70 (1H, dd, J=7.96 Hz, 1.46 Hz), 7.16 (1H, dd, J=7.96 Hz), 7.42(1 h, dd, J=7.96 Hz, 1.46 Hz)]

4) Nine and one tenth grams (9.1 g) of compound [1d] was dissolved in 100 mL of chloroform. Under ice cooling, 12 g of metachloro perbenzoic acid was then incorporated and stirred for 24 hours. Subsequently, ethyl acetate was incorporated to the reaction mixture and washed by utilizing a saturated aqueous solution of potassium carbonate. The resultant was dried and concentrated, and the obtained crystals were washed with isopropyl alcohol to obtain 10.3 g of compound [1e].

[$^1$H-NMR(250 MHz, CDCl$_3$, TMS δ (ppm)) 3.48(3H, s), 5.71(2H, s), 6.63 to 6.66(1H, m), 7.01(1H, s), 7.14(1H, dd, J=7.96 Hz), 7.39 to 7.43(1H, m)]

5) Under ice cooling, ammonia gas was blown into a 40 mL isopropanol suspension comprising 4.6 g of compound [1e] for 15 minutes. The reaction was poured into water and extracted with diethyl ether. The organic layer was washed by means of diluted hydrochloric acid, dried, and concentrated. The obtained crystals were then washed with diethyl ether to result in 1.86 g of compound [1f]. m.p.; 209.2° C. (decomposition)

6) One and one-half grams (1.50 g) of compound [1f] was incorporated to a mixture comprising 15 g of 40% aqueous chloroacetoaldehyde and 7.5 g dioxane, and heated under reflux for 3 hours. The reaction mixture was then cooled with ice, and the precipitated crystals were collected by filtration. The crystals were dissolved in t-butylmethyl ether, dried, concentrated, and the obtained residue was subjected to silica gel chromatography ( eluent; chloroform and chloroform: ethyl acetate=20:1) in order to result in 0.31 g of compound [1 g] (the present invention compound 2-1).

m.p.; 191.5° C.

PRODUCTION EXAMPLE 2 (the production of the present invention compound 1-1)

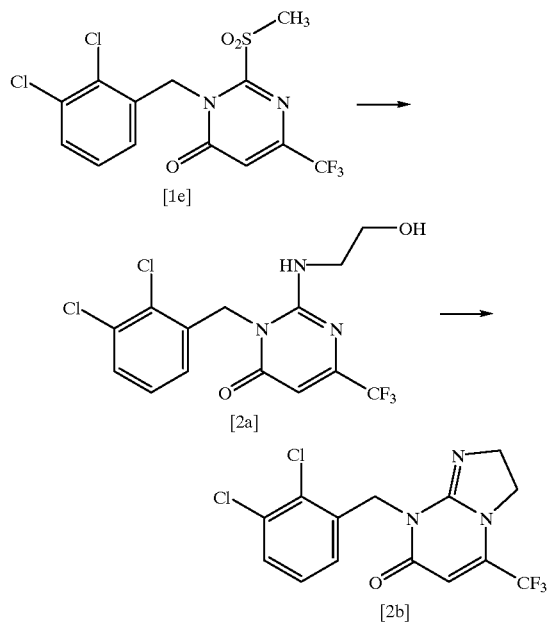

1) Under ice cooling, 3.3 g of compound [1e] was incorporated into 20 mL of ethanolamine and left overnight at room temperature. The reaction mixture was then poured into water, and the precipitated crystals were collected by filtration. The crystals were washed by utilizing water and then dried to provide 1.02 g of compound [2a].

m.p.; 259.3° C. (decomposition)

2) Nine-tenths grams (0.9 g) of compound [2a] was incorporated into 5 g of polyphosphate and stirred for 4 hours at 100° C. to 120° C. The reaction mixture was poured into ice water and filtered to remove the precipitated crystals. The filtrate was then neutralized with a saturated aqueous solution of sodium hydrogencarbonate and extracted with ethyl acetate. The organic layer was dried and concentrated to obtain 77 mg of compound [2b] (the present invention compound 1-1).

m.p.; 139.7° C. Production Example 3 (the production of the present invention compound 3-1)

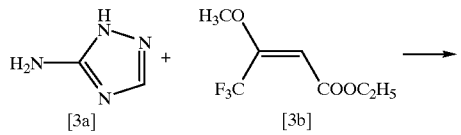

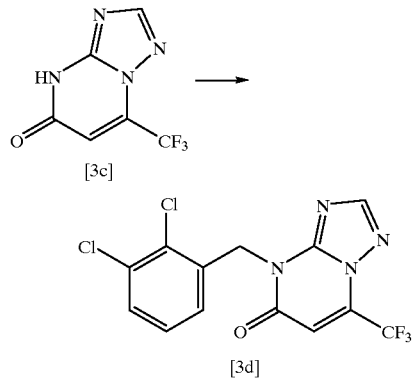

1.) 4.6Grams of compound [3a] and 10 g of compound [3b] were dissolved in 10 mL of ethanol, and the mixture was heated under reflux for 3 hours. The reaction mixture was then cooled to room temperature, extracted, and the precipitated crystals were removed by filtration. The filtrate was concentrated to obtain 6.7 g of a crude compound [3c].

2.) Six and seven-tenths grams (6.7 g) of the crude compound [3c] was dissolved in 60 mL of DMF, 5.0 g of potassium carbonate and 8.7 g of 2,3-dichlorobenzylbromide were added therein and the mixture was left overnight. To the mixture, diluted hydrochloric acid was added and the obtained mixture was extracted with ethyl acetate. The organic layer obtained was washed by utilizing a saturated aqueous solution of sodium chloride, dried by utilizing magnesium sulfate, and concentrated. The residue was subjected to silica gel chromatography (eluent; hexane:ethyl acetate=3:1) to obtain 0.55 g of compound [3d] (present invention compound 3-1.)

m.p. 149.5° C.

Hereinafter, examples of the present inventive compounds are given in Tables 1 through 4 with their compound numbers, but the present inventive compounds are not limited thereto.

Examples of the compound represented by the following formula:

TABLE 1

| compound # | $R^1$ | $R^2$ | $R^3$ | $R^4$ | $R^5$ | $R^6$ |
|---|---|---|---|---|---|---|
| 1-1 | Cl | Cl | H | H | H | $CF_3$ |
| 1-2 | Cl | H | H | H | H | $CF_3$ |
| 1-3 | H | Cl | H | H | H | $CF_3$ |
| 1-4 | H | H | Cl | H | H | $CF_3$ |
| 1-5 | H | H | H | Cl | H | $CF_3$ |
| 1-6 | $CH_3$ | H | H | H | H | $CF_3$ |
| 1-7 | H | $CH_3$ | H | H | H | $CF_3$ |
| 1-8 | H | H | $CH_3$ | H | H | $CF_3$ |
| 1-9 | H | H | H | $CH_3$ | H | $CF_3$ |
| 1-10 | $CF_3$ | H | H | H | H | $CF_3$ |
| 1-11 | H | $CF_3$ | H | H | H | $CF_3$ |
| 1-12 | H | H | $CF_3$ | H | H | $CF_3$ |
| 1-13 | H | H | H | $CF_3$ | H | $CF_3$ |

TABLE 1-continued

| compound # | $R^1$ | $R^2$ | $R^3$ | $R^4$ | $R^5$ | $R^6$ |
|---|---|---|---|---|---|---|
| 1-14 | Cl | H | Cl | H | H | $CF_3$ |
| 1-15 | Cl | H | H | Cl | H | $CF_3$ |
| 1-16 | H | Cl | Cl | H | H | $CF_3$ |
| 1-17 | H | Cl | H | Cl | H | $CF_3$ |
| 1-18 | H | H | Cl | Cl | H | $CF_3$ |
| 1-19 | Cl | Cl | Cl | H | H | $CF_3$ |
| 1-20 | Cl | Cl | H | Cl | H | $CF_3$ |
| 1-21 | Cl | Cl | $CH_3$ | H | H | $CF_3$ |
| 1-22 | Cl | Cl | H | $CH_3$ | H | $CF_3$ |
| 1-23 | Cl | Cl | $CF_3$ | H | H | $CF_3$ |
| 1-24 | Cl | Cl | H | $CF_3$ | H | $CF_3$ |
| 1-25 | Cl | Cl | $OCH_3$ | H | H | $CF_3$ |

TABLE 2

| compound# | $R^1$ | $R^2$ | $R^3$ | $R^4$ | $R^5$ | $R^6$ |
|---|---|---|---|---|---|---|
| 1-26 | Cl | Cl | H | $OCH_3$ | H | $CF_3$ |
| 1-27 | Cl | Cl | $CH_2OCH_3$ | H | H | $CF_3$ |
| 1-28 | Cl | Cl | H | $CH_2OCH_3$ | H | $CF_3$ |
| 1-29 | Cl | Cl | $OCH(CH_3)_2$ | H | H | $CF_3$ |
| 1-30 | Cl | Cl | H | $OCH(CH_3)_2$ | H | $CF_3$ |
| 1-31 | Cl | Cl | $NO_2$ | H | H | $CF_3$ |
| 1-32 | Cl | Cl | H | $NO_2$ | H | $CF_3$ |
| 1-33 | Cl | Cl | $NH_2$ | H | H | $CF_3$ |
| 1-34 | Cl | Cl | H | $NH_2$ | H | $CF_3$ |
| 1-35 | Cl | Cl | H | H | H | $CF_2Cl$ |
| 1-36 | Cl | Cl | H | H | $CH_3$ | $CF_2Cl$ |
| 1-37 | Cl | Cl | H | H | $CH_3$ | $CF_3$ |

Examples of the compound represented by the following formula:

TABLE 3

| compound # | $R^1$ | $R^2$ | $R^3$ | $R^4$ | $R^5$ | $R^6$ |
|---|---|---|---|---|---|---|
| 2-1 | Cl | Cl | H | H | H | $CF_3$ |
| 2-2 | Cl | H | H | H | H | $CF_3$ |
| 2-3 | H | Cl | H | H | H | $CF_3$ |
| 2-4 | H | H | Cl | H | H | $CF_3$ |
| 2-5 | H | H | H | Cl | H | $CF_3$ |
| 2-6 | $CH_3$ | H | H | H | H | $CF_3$ |
| 2-7 | H | $CH_3$ | H | H | H | $CF_3$ |
| 2-8 | H | H | $CH_3$ | H | H | $CF_3$ |
| 2-9 | H | H | H | $CH_3$ | H | $CF_3$ |
| 2-10 | $CF_3$ | H | H | H | H | $CF_3$ |
| 2-11 | H | $CF_3$ | H | H | H | $CF_3$ |
| 2-12 | H | H | $CF_3$ | H | H | $CF_3$ |
| 2-13 | H | H | H | $CF_3$ | H | $CF_3$ |
| 2-14 | Cl | H | Cl | H | H | $CF_3$ |

TABLE 3-continued

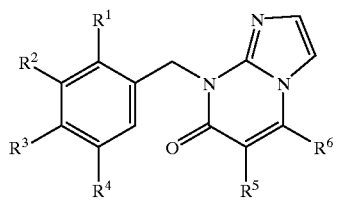

| compound # | R¹ | R² | R³ | R⁴ | R⁵ | R⁶ |
|---|---|---|---|---|---|---|
| 2-15 | Cl | H | H | Cl | H | CF₃ |
| 2-16 | H | Cl | Cl | H | H | CF₃ |
| 2-17 | H | Cl | H | Cl | H | CF₃ |
| 2-18 | H | H | Cl | Cl | H | CF₃ |
| 2-19 | Cl | Cl | Cl | H | H | CF₃ |
| 2-20 | Cl | Cl | H | Cl | H | CF₃ |
| 2-21 | Cl | Cl | CH₃ | H | H | CF₃ |
| 2-22 | Cl | Cl | H | CH₃ | H | CF₃ |
| 2-23 | Cl | Cl | CF₃ | H | H | CF₃ |
| 2-24 | Cl | Cl | H | CF₃ | H | CF₃ |
| 2-25 | Cl | Cl | OCH₃ | H | H | CF₃ |

TABLE 4

| compound# | R¹ | R² | R³ | R⁴ | R⁵ | R⁶ |
|---|---|---|---|---|---|---|
| 2-26 | Cl | Cl | H | OCH₃ | H | CF₃ |
| 2-27 | Cl | Cl | CH₂OCH₃ | H | H | CF₃ |
| 2-28 | Cl | Cl | H | CH₂OCH₃ | H | CF₃ |
| 2-29 | Cl | Cl | OCH(CH₃)₂ | H | H | CF₃ |
| 2-30 | Cl | Cl | H | OCH(CH₃)₂ | H | CF₃ |
| 2-31 | Cl | Cl | NO₂ | H | H | CF₃ |
| 2-32 | Cl | Cl | H | NO₂ | H | CF₃ |
| 2-33 | Cl | Cl | NH₂ | H | H | CF₃ |
| 2-34 | Cl | Cl | H | NH₂ | H | CF₃ |
| 2-35 | Cl | Cl | H | H | H | CF₂Cl |
| 2-36 | Cl | Cl | H | H | CH₃ | CF₂Cl |
| 2-37 | Cl | Cl | H | H | CH₃ | CF₃ |

TABLE 5

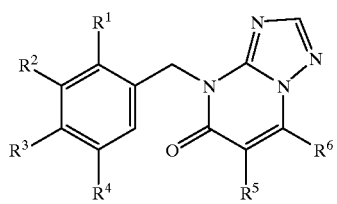

| compound # | R¹ | R² | R³ | R⁴ | R⁵ | R⁶ |
|---|---|---|---|---|---|---|
| 3-1 | Cl | Cl | H | H | H | CF₃ |
| 3-2 | Cl | H | H | H | H | CF₃ |
| 3-3 | H | Cl | H | H | H | CF₃ |
| 3-4 | H | H | Cl | H | H | CF₃ |
| 3-5 | H | H | H | Cl | H | CF₃ |
| 3-6 | CH₃ | H | H | H | H | CF₃ |
| 3-7 | H | CH₃ | H | H | H | CF₃ |
| 3-8 | H | H | CH₃ | H | H | CF₃ |
| 3-9 | H | H | H | CH₃ | H | CF₃ |
| 3-10 | CF₃ | H | H | H | H | CF₃ |
| 3-11 | H | CF₃ | H | H | H | CF₃ |
| 3-12 | H | H | CF₃ | H | H | CF₃ |
| 3-13 | H | H | H | CF₃ | H | CF₃ |
| 3-14 | Cl | H | Cl | H | H | CF₃ |
| 3-15 | Cl | H | H | Cl | H | CF₃ |
| 3-16 | H | Cl | Cl | H | H | CF₃ |
| 3-17 | H | Cl | H | Cl | H | CF₃ |
| 3-18 | H | H | Cl | Cl | H | CF₃ |

TABLE 5-continued

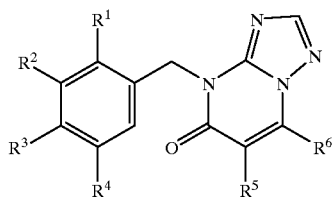

| compound # | R¹ | R² | R³ | R⁴ | R⁵ | R⁶ |
|---|---|---|---|---|---|---|
| 3-19 | Cl | Cl | Cl | H | H | CF₃ |
| 3-20 | Cl | Cl | H | Cl | H | CF₃ |
| 3-21 | Cl | Cl | CH₃ | H | H | CF₃ |
| 3-22 | Cl | Cl | H | CH₃ | H | CF₃ |
| 3-23 | Cl | Cl | CF₃ | H | H | CF₃ |
| 3-24 | Cl | Cl | H | CF₃ | H | CF₃ |
| 3-25 | Cl | Cl | OCH₃ | H | H | CF₃ |

TABLE 6

| compound# | R¹ | R² | R³ | R⁴ | R⁵ | R⁶ |
|---|---|---|---|---|---|---|
| 3-26 | Cl | Cl | H | OCH₃ | H | CF₃ |
| 3-27 | Cl | Cl | CH₂OCH₃ | H | H | CF₃ |
| 3-28 | Cl | Cl | H | CH₂OCH₃ | H | CF₃ |
| 3-29 | Cl | Cl | OCH(CH₃)₂ | H | H | CF₃ |
| 3-30 | Cl | Cl | H | OCH(CH₃)₂ | H | CF₃ |
| 3-31 | Cl | Cl | NO₂ | H | H | CF₃ |
| 3-32 | Cl | Cl | H | NO₂ | H | CF₃ |
| 3-33 | Cl | Cl | NH₂ | H | H | CF₃ |
| 3-34 | Cl | Cl | H | NH₂ | H | CF₃ |
| 3-35 | Cl | Cl | H | H | H | CF₂Cl |
| 3-36 | Cl | Cl | H | H | CH₃ | CF₂Cl |
| 3-37 | Cl | Cl | H | H | CH₃ | CF₃ |

Hereinafter, the formulation examples are given. "Parts" represents parts by weight.

Formulation Example 1

Fifty (50) parts of one of the present inventive compounds selected from 1-1 to 1-37, 2-1 to 2-37 or 3-1 to 3-37 is combined with 3 parts of calcium ligninsulfonat 2 parts of sodium laurylsulfate and 45 parts of synthetic hydrated silicon oxide and the combination is pulverized and mixed to obtain a wettable powder of the present invention possessing herbicidal activity.

Formulation Example 2

Ten (10) parts of one of the present inventive compounds selected from 1-1 to 1-37, 2-1 to 2-37 or 3-1 to 3-37 is combined with 14 parts polyoxyethylene styrylph ether, 6 parts of calcium dodecylbenzene sulfonate 35 parts of xylene and 35 parts cyclohexanone, and the combination is mixed to obtain an emulsifiable concentrate of the present invention possessing herbicidal activity.

Formulation Example 3

Two (2) parts of one of the present inventive compounds selected from 1-1 to 1-37, 2-1 to 2-37 or 3-1 to 3-37 is combined with 2 parts of syntheic hydrated sili oxide, 2 parts of calcium ligninsulfonate, 30 parts of bentonite and 64 parts of caolin clay, and the combination is pulverized and mixed. Thereafter water is incorporated, the mixture is kneaded, granulated, and dried to obtain granules of the present invention possessing herbicidal activity.

Formulation Example 4

Twenty-five parts of one of the present inventive compounds selected from 1-1 to 1-37, 2-1 to 2-37 or 3-1 to 3-37 is combined with 50 parts of 10% aqueous polyvinyl alcohol and 25 parts of water, the combination is mixed and wetpulverized until the average diameter thereof becomes 5 μm or less to obtain a flowable of the present invention possessing herbicidal activity.

Formulation Example 5

Into a 10% aqueous solution of polyvinyl alcohol, 5 parts of one of the present inventive compounds selected from 1-1 to 1-37, 2-1 to 2-37 or 3-1 to 3-37 is incorporated. The resulting combination is emulsifiably dispersed with a homogenizer until the average diameter thereof becomes 10 μm or less, and 55 parts of water is added therein to obtain a concentrated emulsion of the present invention possessing herbicidal activity.

Hereinafter, the following test examples are provided, in order to evidence that the present inventive compounds are efficacious as the active ingredient of a herbicidal composition.

Test Example 1

A cylindrical plastic pot having a diameter of 10 cm and a depth of 10 cm was filled with soil and then seeded with velvetleaf (*Abutilon theophrasti*), morningglory (*ipomoea*) and barnyardgrass (*Echinochloa crus-galli*). These test plants were grown in a greenhouse for 14 days. Then, compound 1-1 was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare After the application, the test plants were grown in the greenhouse for 8 days, and the herbicidal activity of the applied composition was determined. As a result, it was determined that the growth of velvet leaf, morningglory and barnyard grass was completely controlled when compound 1-1 was applied at the dosage of 500 g/ha.

Test Example 2

A cylindrical plastic pot having a diameter of 10 cm and a depth of 10 cm was filled with soil and then seeded with velvetleaf (*Abutilon theophrasti*). These test plants were grown in a greenhouse for 14 days. After then, compound 2-1 was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare After the application, the test plants were grown in the greenhouse for 8 days, and the herbicidal activity was examined. As a result, it was determined that the growth of velvet leaf was completely controlled when compound 2-1 was applied at the dosage of 500 g/ha.

Test Example 3

A cylindrical plastic pot having a diameter of 10 cm and a depth of 10 cm was filled with soil and then seeded with velvetleaf (*Abutilon theophrasti*) and ivyleaf morningglory (*Ipomoea hederacea*). These test plants were grown in a greenhouse for 14 days. Then, compound 3-1 was formulated into an emulsifiable concentrate according to Formulation Example 2 and diluted to the prescribed amount with water containing a spreading agent and the dilution was uniformly sprayed over the foliage of the test plants with a sprayer at a rate of 1000 liters per hectare After the application, the test plants were grown in the greenhouse for 8 days, and the herbicidal activity thereof was examined. As a result, the growth of velvet leaf and ivyleaf morningglory was completely controlled when compound 3-1 was applied at the dosage of 2,000 g/ha.

Test Example 4

A cylindrical plastic pot having a diameter of 10 cm and a depth of 10 cm was filled with soil and then seeded with velvetleaf (*Abutilon theophrasti*) and ivyleaf morningglory (*Ipomoea hederacea*). Then, compound 1-1 was formulated into an emulsifiable concentrate according to Formulation Example 2 and then diluted to the prescribed amount with water, and the dilution was uniformly sprayed over the surface of the soil with a sprayer at a rate of 1000 liters per hectare. After the application, the test plants were grown in the greenhouse for 9 days, and the herbicidal activity of the applied composition was examined. The emergence of velvetleaf and ivyleaf morningglory were completely controlled when compound 1-1 was applied at the dosage of 2000 g/ha.

Test Example 5

A cylindrical plastic pot having a diameter of 10 cm and a depth of 10 cm was filled with soil and then seeded with ivyleaf morningglory (*Ipomoea hederacea*). Compound 2-1 was formulated into an emulsifiable concentrate according to Formulation Example 2 and then diluted to the prescribed amount with water and the dilution was uniformly sprayed over the surface of the soil with a sprayer at a rate of 1000 liters per hectare. After the application, the test plants were grown in the greenhouse for 9 days, and the herbicidal activity was examined. Compound 2-1 completely controlled the emergence of ivyleaf morningglory when applied at the dosage of 2000 g/ha.

Test Example 6

A cylindrical plastic pot having a diameter of 10 cm and a depth of 10 cm was filled with soil and then seeded with velvetleaf (*Abutilon theophrasti*). Compound 3-1 was formulated into an emulsifiable concentrate according to Formulation Example 2 and then diluted to the prescribed amount with water and the dilution was uniformly sprayed over the surface of the soil with a sprayer at a rate of 1000 liters per hectare. After the application, the test plants were grown in the greenhouse for 9 days, and the herbicidal activity of the applied composition was examined. Compound 3-1 completely controlled the emergence of velvetleaf when applied at the dosage of 2000 g/ha.

Test Example 7

A cylindrical plastic pot having a diameter of 9 cm and a depth of 11 cm was filled with soil and then seeded with barnyardgrass (*Echinochloa oryzicola*) and hardstem bulrush (*Scirpus juncoides*). After flooding the said pot until a paddy-field condition was obtained, the test plant was grown in a greenhouse. Twelve (12) days later, compound 1-1 was formulated into an emulsifiable concentrate according to Formulation Example 2, diluted to the prescribed amount with water, and was then applied onto the surface of the water at a rate of 50L per are. After the application, the test plants were grown in the greenhouse for 9 days and the herbicidal activity was examined. The growth of barnyadgrass and hardstem bulrush was completely controlled when compound 1-1 was applied at the dosage of 500 g/ha.

Test Example 8

A cylindrical plastic pot having a diameter of 9 cm and a depth of 11 cm was filled with soil and then seeded with barnyardgrass (*Echinochloa oryzicola*). After flooding the pot until a paddy-field condition was obtained, the test plant was grown in a greenhouse. Twelve (12) days later, compound 2-1 and compound 3-1 were formulated into an emulsifiable concentrate according to Formulation Example 2, respectively, diluted to the prescribed amount with water, and was then applied onto the surface of water at a rate of 50L per are. After the application, the test plants were grown in the greenhouse for 9 days, and the herbicidal activity was examined. The growth of barnyardgrass was completely controlled when applied at the dosage of 500 g/ha of compound 2-1 and 3-1, respectively.

By utilizing the present invention compound, an excellent herbicidal efficacy can be obtained.

What is claimed is:

1. A pyrimidinone compound encompassed by the following formula:

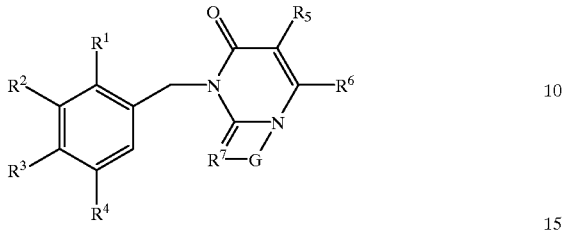

wherein, $R^1$ represents hydrogen, halogen, $C_1$–$C_3$ alkyl or $C_1$–$C_3$ haloalkyl;

$R^2$ represents hydrogen, halogen, $C_1$–$C_6$ alkyl, $C_1$–$C_6$ haloalkyl, $OR^8$, $SR^9$, $NHR^{10}$, $COOR^{11}$, $COR^{12}$, $SO_2R^{13}$, $NO_2$ or CN;

$R^3$ represents hydrogen, halogen, $C_1$–$C_6$ alkyl, $C_1$–$C_6$ haloalkyl, $C_1$–$C_3$ alkoxy $C_1$–$C_3$ alkyl, $OR^8$, $SR^9$, $NHR^{10}$, $COOR^{11}$, $COR^{12}$, $SO_2R^{13}$, $C(R^{12})\!=\!C(R^{14})(R^{15})$, $NO_2$ or CN;

$R^4$ represents hydrogen, halogen, $C_1$–$C_6$ alkyl, $C_1$–$C_6$ haloalkyl, $C_1$–$C_3$ alkoxy $C_1$–$C_3$ alkyl, $OR^8$, $SR^9$, $NHR^{10}$, $COOR^{11}$, $COR^{12}$, $SO_2R^{13}$, $CH\!=\!C(R^{14})(R^{15})$, $C(R^{16})\!=\!NOR^{17}$, $NO_2$ or CN;

$R^5$ represents hydrogen, halogen or $C_1$–$C_3$ alkyl;

$R^6$ represents $C_1$–$C_3$ alkyl or $C_1$–$C_3$ haloalkyl;

$R^7$ represents nitrogen or CH;

in which $R^8$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ halocycloalkyl, $C_3$–$C_{10}$ cycloalkenyl, $C_3$–$C_{10}$ halocycloalkenyl, $C_1$–$C_5$ alkylcarbonyl, $C_1$–$C_5$ haloalkylcarbonyl, $C_3$–$C_6$ cycloalkylcarbonyl, $C_3$–$C_6$ halocycloalkylcarbonyl, $C_1$–$C_6$ alkylcarbonyl $C_1$–$C_6$ alkyl, $C_1$–$C_6$ haloalkylcarbonyl $C_1$–$C_6$ alkyl, $C_1$–$C_6$ alkylcabonyl $C_1$–$C_6$ haloalkyl, $C_1$–$C_6$ haloalkylcarbonyl $C_1$–$C_6$ haloalkyl, $C_1$–$C_6$ alkoxycarbonyl, $C_1$–$C_6$ haloalkoxycarbonyl, $C_3$–$C_{10}$ cycloalkoxycarbonyl, carboxy $C_1$–$C_5$ alkyl, $C_1$–$C_{10}$ alkoxycarbonyl $C_1$–$C_5$ alkyl, $C_1$–$C_{10}$ haloalkoxycarbonyl $C_1$–$C_5$ alkyl, $C_1$–$C_{10}$ alkoxycarbonyl $C_1$–$C_5$ haloalkyl, $C_1$–$C_{10}$ haloalkoxycarbonyl $C_1$–$C_5$ haloalkyl, $C_3$–$C_{10}$ cycloalkoxycarbonyl $C_1$–$C_5$ alkyl, $C_3$–$C_{10}$ halocycloalkoxycarbonyl $C_1$–$C_5$ alkyl, $C_3$–$C_{10}$ halocycloalkoxycarbonyl $C_1$–$C_5$ haloalkyl, $C_3$–$C_{10}$ cycloalkoxycarbonyl $C_1$–$C_5$ haloalkyl, $C_1$–$C_6$ alkoxy $C_1$–$C_6$ alkyl, $C_1$–$C_6$ alkoxy $C_1$–$C_6$ haloalkyl, $C_1$–$C_6$ haloalkoxy $C_1$–$C_6$ alkyl, $C_1$–$C_6$ haloalkoxy $C_1$–$C_6$ haloalkyl, $C_1$–$C_6$ alkylthio $C_1$–$C_6$ alkyl, $C_1$–$C_6$ alkylthio $C_1$–$C_6$ haloalkyl, $C_1$–$C_6$ haloalkylthio $C_1$–$C_6$ alkyl, $C_1$–$C_6$ haloalkylthio $C_1$–$C_6$ haloalkyl, cyano $C_1$–$C_4$ alkyl, aryl that may have substituent(s), aryl $C_1$–$C_3$ alkyl that may have substituent(s) or arylcarbonyl that may have substituent(s);

$R^9$ represents hydrogen, $C_1$–$C_{10}$ alkyl, $C_1$–$C_{10}$ haloalkyl, $C_3$–$C_8$ alkenyl, $C_3$–$C_8$ haloalkenyl, $C_3$–$C_8$ alkynyl, $C_3$–$C_8$ haloalkynyl, $C_3$–$C_{10}$ cycloalkyl, $C_3$–$C_{10}$ halocycloalkyl, $C_3$–$C_{10}$ cycloalkenyl, $C_3$–$C_{10}$ halocycloalkenyl, $C_1$–$C_5$ alkylcarbonyl, $C_1$–$C_5$ haloalkylcarbonyl, $C_3$–$C_6$ cycloalkylcarbonyl, $C_3$–$C_6$ halocycloalkylcarbonyl, $C_1$–$C_6$ alkylcarbonyl $C_1$–$C_6$ alkyl, $C_1$–$C_6$ haloalkylcarbonyl $C_1$–$C_6$ alkyl, $C_1$–$C_6$ alkylcarbonyl $C_1$–$C_6$ haloalkyl, $C_1$–$C_6$ haloalkylcarbonyl $C_1$–$C_6$ haloalkyl, $C_1$–$C_6$ alkoxycarbonyl, $C_1$–$C_6$ haloalkoxycarbonyl, $C_3$–$C_{10}$ cycloalkoxycarbonyl, carboxy $C_1$–$C_5$ alkyl, $C_1$–$C_{10}$ alkyoxycarbonyl $C_1$–$C_5$ alkyl, $C_1$–$C_{10}$ haloalkoxycarbonyl $C_1$–$C_5$ alkyl, $C_1$–$C_{10}$ alkoxycarbonyl $C_1$–$C_5$ haloalkyl, $C_1$–$C_{10}$ haloalkoxycarbonyl $C_1$–$C_5$ haloalkyl, $C_3$–$C_{10}$ cycloalkoxycarbonyl $C_1$–$C_5$ alkyl, $C_3$–$C_{10}$ halocycloalkoxycarbonyl $C_1$–$C_5$ alkyl, $C_3$–$C_{10}$ halocycloalkoxycarbonyl $C_1$–$C_5$ haloalkyl, $C_3$–$C_{10}$ cycloalkoxycarbonyl $C_1$–$C_5$ haloalkyl, $C_1$–$C_6$ alkoxy $C_1$–$C_6$ alkyl, $C_1$–$C_6$ alkoxy $C_1$–$C_6$ haloalkyl, $C_1$–$C_6$ haloalkoxy $C_1$–$C_6$ alkyl, $C_1$–$C_6$ haloalkoxy $C_1$–$C_6$ haloalkyl, $C_1$–$C_6$ alkylthio $C_1$–$C_6$ alkyl, $C_1$–$C_6$ alkylthio $C_1$–$C_6$ haloalkyl, $C_1$–$C_6$ haloalkylthio $C_1$–$C_6$ alkyl, $C_1$–$C_6$ haloalkylthio $C_1$–$C_6$ haloalkyl, cyano $C_1$–$C_4$ alkyl, aryl that may have substituent(s), aryl $C_1$–$C_3$ alkyl that may have substituent(s), arylcarbonyl that may have substituent(s), $SR^{18}$, $SOR^{19}$ or $SO_2R^{20}$;

$R^{11}$ represents hydrogen, $C_1$–$C_{10}$ alkyl, $C_1$–$C_{10}$ haloalkyl, $C_3$–$C_8$ cycloalkyl, $C_3$–$C_8$ halocycloalkyl, $N(R^{21})(R^{22})$, $N\!=\!C(R^{21})(R^{22})$, carboxy $C_1$–$C_3$ alkyl, $C_1$–$C_5$ alkoxycarbonyl $C_1$–$C_3$ alkyl, $C_1$–$C_5$ haloalkoxycarbonyl $C_1$–$C_3$ alkyl, $C_3$–$C_6$ cycloalkoxycarbonyl $C_1$–$C_3$ alkyl or $C_3$–$C_8$ alkenyloxycarbonyl $C_1$–$C_3$ alkyl;

$R^{12}$ represents hydrogen, chlorine, $C_1$–$C_5$ alkyl, $C_1$–$C_5$ haloalkyl, $C_3$–$C_6$ cycloalkyl, $C_3$–$C_6$ halocycloalkyl or $N(R^{23})(R^{24})$;

$R^{13}$ represents chlorine, $C_1$–$C_{10}$ alkyl, $C_1$–$C_{10}$ haloalkyl, $N(R^{25})(R^{26})$ or $OR^{27}$;

$R^{14}$ represents hydrogen, halogen or $C_1$–$C_3$ alkyl;

$R^{15}$ represents hydrogen, $COOR^{28}$ or CN;

$R^{16}$ represents hydrogen, halogen, $C_1$–$C_4$ alkyl, $C_1$–$C_4$ haloalkyl, $C_3$–$C_5$ cycloalkyl or $C_3$–$C_5$ halocycloalkyl;

$R^{17}$ represents hydrogen, $C_1$–$C_{10}$ alkyl, $C_1$–$C_{10}$ haloalkyl, $C_3$–$C_6$ cycloalkyl, $C_3$–$C_6$ halocycloalkyl, $C_3$–$C_5$ alkenyl, $C_3$–$C_5$ haloalkenyl, $C_3$–$C_5$ alkynyl, $C_3$–$C_5$ haloalkynyl, carboxy $C_1$–$C_3$ alkyl, $C_1$–$C_5$ alkoxycarbonyl $C_1$–$C_3$ alkyl, aryl that may have substituent(s) or aryl $C_1$–$C_3$ alkyl that may have substituent(s);

$R^{18}$ represents $C_1$–$C_{10}$ alkyl, $C_1$–$C_{10}$ haloalkyl or aryl that may have substituent(s);

$R^{19}$ represents $C_1$–$C_{10}$ alkyl, $C_1$–$C_{10}$ haloalkyl, $C_3$–$C_8$ cycloalkyl, $C_3$–$C_8$ halocycloalkyl or aryl that may have substituent(s);

$R^{20}$ represents $C_1$–$C_{10}$ alkyl, $C_1$–$C_{10}$ haloalkyl, $C_3$–$C_8$ cycloalkyl, $C_3$–$C_8$ halocycloalkyl or aryl that may have substituent(s);

$R^{21}$ represents hydrogen or $C_1$–$C_5$ alkyl;

$R^{22}$ represents hydrogen, $C_1$–$C_5$ alkyl, $C_1$–$C_5$ haloalkyl or aryl that may have substituent(s);

$R^{23}$ represents hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl or aryl that may have substituent(s);

$R^{24}$ represents hydrogen, $C_1$–$C_{10}$ alkyl, or $C_1$–$C_{10}$ haloalkyl;

$R^{25}$ represents hydrogen, $C_1$–$C_5$ alkyl or $C_1$–$C_5$ haloalkyl;

$R^{26}$ represents hydrogen, $C_1$–$C_{10}$ alkyl, or $C_1$–$C_{10}$ haloalkyl;

$R^{27}$ represents $C_1$–$C_{10}$ alkyl;

$R^{28}$ represents hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl or aryl that may have substituent(s); and G represents G-1, or G-3 given in the formula:

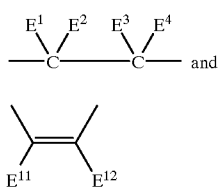

wherein $E^1$, $E^2$, $E^3$, $E^4$, $E^5$, $E^6$, $E^7$, $E^8$, $E^9$, $E^{10}$, $E^{11}$, $E^{12}$, $E^{13}$ or $E^{14}$ each represent hydrogen, halogen or $C_1$–$C_3$ alkyl.

2. The pyrimidinone compound recited in claim 1, wherein the aryl of the aryl that may have substituent(s), the aryl $C_1$–$C_3$ alkyl that may have substituent(s) or the arylcarbonyl that may have substituent(s) in the definitions of $R^8$, $R^9$, $R^{10}$, $R^{17}$, $R^{18}$, $R^{19}$, $R^{20}$, $R^{22}$ and $R^{23}$ is phenyl that may have, same or different, at least one substituent selected from the group consisting of halogen, $C_1$–$C_6$ alkyl, $C_1$–$C_6$ haloalkyl, $C_1$–$C_6$ alkoxy, $C_1$–$C_6$ haloalkoxy, —$NO_2$ and CN.

3. The pyrimidinone compound recited in claim 1, wherein $R^1$ is hydrogen or halogen.

4. The pyrimidinone compound recited in claim 1, wherein $R^2$ is hydrogen or halogen.

5. The pyrimidinone compound recited in claim 1, wherein $R^3$ is hydrogen, halogen, $C_1$–$C_6$ alkyl, $C_1$–$C_6$ haloalkyl, $OR^8$, $NHR^{10}$, $COOR^{11}$, $COR^{12}$, $NO_2$ or CN.

6. The pyrimidinone compound recited in claim 1, wherein $R^4$ is hydrogen, halogen, $C_1$–$C_6$ alkyl, $C_1$–$C_6$ haloalkyl, $OR^8$, $SR^9$, $NR^{10}$, $COOR^{11}$, $COR^{12}$, $NO_2$ or CN.

7. The pyrimidinone compound recited in claim 1, wherein $R^5$ is hydrogen.

8. The pyrimidinone compound recited in claim 1, wherein $R^6$ is $C_1$–$C_3$ haloalkyl.

9. The pyrimidinone compound recited in claim 1, wherein $R^7$ is nitrogen.

10. The pyrimidinone compound recited in claim 1, wherein $R^7$ is CH.

11. The pyrimidinone compound recited in claim 1, wherein G is G-1.

12. The pyrimidinone compound recited in claim 1, wherein G is G-3.

13. The pyrimidinone compound recited in claim 1, wherein $R^6$ is trifluoromethyl.

14. The pyrimidinone compound recited in claim 1, wherein $R^6$ is chlorodifluoromethyl.

15. The pyrimidinone compound recited in claim 1, wherein $R^1$ and $R^2$ are halogen.

16. The pyrimidinone compound recited in claim 15, wherein $R^6$ is trifluoromethyl.

17. A herbicidal composition, which comprises the pyrimidinone compound recited in of claim 1 as an active ingredient and an agrochemically acceptable carrier therefor.

18. A method for controlling weeds which comprises applying an effective amount of a pyrimidinone compound as recited in claim 1 to weeds or the locus in which weeds grow or will grow.

* * * * *